United States Patent
Witschi et al.

(10) Patent No.: US 9,643,928 B2
(45) Date of Patent: May 9, 2017

(54) CRYSTALLINE FORMS OF {[1-CYANO-5-(4-CHLOROPHENOXY)-4-HYDROXY-ISOQUINOLINE-3-CARBONYL]-AMINO}-ACETIC ACID

(71) Applicant: FIBROGEN, INC., San Francisco, CA (US)

(72) Inventors: Claudia Witschi, San Francisco, CA (US); Michael D. Thompson, Redwood City, CA (US); Jung Min Park, San Francisco, CA (US); Michael P. Arend, Foster City, CA (US)

(73) Assignee: FibroGen, Inc., San Francisco, CA (US)

( * ) Notice: Subject to any disclaimer, the term of this patent is extended or adjusted under 35 U.S.C. 154(b) by 0 days.

(21) Appl. No.: 14/763,127

(22) PCT Filed: Jan. 23, 2014

(86) PCT No.: PCT/US2014/012780
§ 371 (c)(1),
(2) Date: Jul. 23, 2015

(87) PCT Pub. No.: WO2014/116849
PCT Pub. Date: Jul. 31, 2014

(65) Prior Publication Data
US 2016/0002170 A1   Jan. 7, 2016

Related U.S. Application Data

(60) Provisional application No. 61/756,361, filed on Jan. 24, 2013.

(51) Int. Cl.
C07D 217/26   (2006.01)
A61K 31/472   (2006.01)

(52) U.S. Cl.
CPC .................. *C07D 217/26* (2013.01)

(58) Field of Classification Search
None
See application file for complete search history.

(56) References Cited

U.S. PATENT DOCUMENTS

| | | | |
|---|---|---|---|
| 3,989,704 A | 11/1976 | Houlihan et al. |
| 4,036,964 A | 7/1977 | Buckle et al. |
| 4,260,611 A | 4/1981 | Bartmann et al. |
| 4,559,403 A | 12/1985 | Bruderer et al. |
| 4,584,379 A | 4/1986 | Wagner |
| 4,673,682 A | 6/1987 | Konz et al. |
| 4,822,800 A | 4/1989 | Falotico et al. |
| 4,952,588 A | 8/1990 | Glamkowski et al. |
| 4,966,906 A | 10/1990 | Glamkowski et al. |
| 5,620,995 A | 4/1997 | Weidmann et al. |
| 5,658,933 A | 8/1997 | Weidmann et al. |
| 5,719,164 A | 2/1998 | Weidmann et al. |
| 6,093,730 A | 7/2000 | Weidmann et al. |
| 6,319,931 B1 | 11/2001 | Kroemer et al. |
| 6,358,973 B1 | 3/2002 | Napoletano et al. |
| 6,358,976 B1 | 3/2002 | Wityak et al. |
| 6,369,053 B1 | 4/2002 | Yuan et al. |
| 6,762,318 B2 | 7/2004 | Kodra et al. |
| 6,777,425 B2 | 8/2004 | Burli et al. |
| 6,903,114 B2 | 6/2005 | Backstrom et al. |
| 7,208,601 B2 | 4/2007 | Mjalli et al. |
| 7,248,053 B2 | 7/2007 | Houldsworth |
| 7,294,457 B2 | 11/2007 | Kukolj et al. |
| 7,323,475 B2 | 1/2008 | Arend et al. |
| 7,928,120 B2 | 4/2011 | Arend et al. |
| 8,017,625 B2 | 9/2011 | Arend et al. |
| 2003/0153503 A1 | 8/2003 | Klaus et al. |
| 2003/0176317 A1 | 9/2003 | Guenzler-Pukall et al. |
| 2004/0204356 A1 | 10/2004 | Guenzler-Pukall et al. |
| 2004/0235082 A1 | 11/2004 | Fourney et al. |
| 2005/0020487 A1 | 1/2005 | Klaus et al. |
| 2006/0035965 A1 | 2/2006 | Dalton et al. |
| 2006/0178316 A1 | 8/2006 | Klaus et al. |
| 2006/0178317 A1 | 8/2006 | Klaus et al. |
| 2006/0183695 A1 | 8/2006 | Klaus et al. |
| 2006/0199836 A1 | 9/2006 | Turtle et al. |
| 2006/0217416 A1 | 9/2006 | Arend et al. |
| 2006/0251638 A1 | 11/2006 | Guenzler-Pukall |
| 2006/0258660 A1 | 11/2006 | Guenzler-Pukall et al. |
| 2006/0258702 A1 | 11/2006 | Guenzler-Pukall et al. |
| 2006/0270699 A1 | 11/2006 | Guenzler-Pukall et al. |
| 2006/0276477 A1 | 12/2006 | Klaus et al. |
| 2007/0004627 A1 | 1/2007 | Seeley et al. |
| 2007/0155784 A1 | 7/2007 | Arend et al. |

(Continued)

FOREIGN PATENT DOCUMENTS

| CA | 2134866 | 5/1995 |
|---|---|---|
| EP | 532466 | 3/1993 |

(Continued)

OTHER PUBLICATIONS

Morissette et al, Advanced Drug Delivery Reviews, 56 (2004), pp. 275-300.*
Bickel et al. "Selective Inhibition of Hepatic Collagen Accumulation in Experimental Liver Fibrosis in Rats by a New Prolyl 4-Hydroxylase Inhibitor", *Hepatology*, 28:404-411 (1998).
Caira, "Crystalline Polymorphism of Organic Compounds", *Topics in Current Chemistry*, Jan. 1, 1998, pp. 163-208, vol. 198, Berlin, Germany.
Cockman et al., "Hypoxia Inducible Factor-alpha Binding and Ubiquitylation by the von Hippel-Lindau Tumor Suppressor Protein", *J. Biol. Chem.*, 275:25733-25741 (2000).

(Continued)

*Primary Examiner* — Zinna Northington Davis
(74) *Attorney, Agent, or Firm* — Leanne C. Price; Sheppard Mullin Richter & Hampton LLP

(57) ABSTRACT

The present disclosure relates to crystalline forms of {[1-cyano-5-(4-chlorophenoxy)-4-hydroxy-isoquinoline-3-carbonyl]-amino}-acetic acid (Compound A), the process of preparing crystalline forms of Compound A, the pharmaceutical compositions containing them, and the methods of use thereof.

39 Claims, 12 Drawing Sheets

(56) References Cited

U.S. PATENT DOCUMENTS

| | | |
|---|---|---|
| 2007/0185159 A1 | 8/2007 | Arend et al. |
| 2007/0292433 A1 | 12/2007 | Seeley et al. |
| 2007/0293575 A1 | 12/2007 | Seeley et al. |
| 2008/0004309 A1 | 1/2008 | Deng et al. |

FOREIGN PATENT DOCUMENTS

| | | |
|---|---|---|
| EP | 0650960 | 9/1994 |
| EP | 0650961 | 10/1994 |
| EP | 626178 | 11/1994 |
| EP | 706795 | 4/1996 |
| EP | 0911340 | 4/1999 |
| EP | 1676834 | 7/2006 |
| JP | A-H07-224039 | 8/1995 |
| JP | A-H07-228571 | 8/1995 |
| JP | A-H11-302257 | 11/1999 |
| WO | WO 96/18616 | 6/1996 |
| WO | WO 98/50343 | 11/1998 |
| WO | WO 98/50346 | 11/1998 |
| WO | WO 01/58892 | 8/2001 |
| WO | WO 02/070510 | 9/2002 |
| WO | WO 02/074981 | 9/2002 |
| WO | WO 02/100832 | 12/2002 |
| WO | WO 02/101073 | 12/2002 |
| WO | WO 03/007945 | 1/2003 |
| WO | WO 03/010141 | 2/2003 |
| WO | WO 03/014377 | 2/2003 |
| WO | WO 03/049686 | 6/2003 |
| WO | WO 03/080566 | 10/2003 |
| WO | WO 2004/108681 | 12/2004 |
| WO | WO 2005/009962 | 2/2005 |
| WO | WO 2005/014533 | 2/2005 |
| WO | WO 2007/090068 | 8/2007 |
| WO | WO 2009/075826 | 6/2009 |
| WO | WO 2014/116849 | 7/2014 |

OTHER PUBLICATIONS

Denker, "Erythropoietin: From Bench to Bedside", *Nephrology*, vol. 2, Issue 3, Mar. 2004, 6 pages.
Franklin et al., "Inhibition of prolyl 4-hydroxylase in vitro and in vivo by members of a novel series of phenanthrolinones" *Biochem J.*, 353:333-338 (2001).
Franklin, et al. "Approaches to the design of anti-fibrotic drugs" *Biochem. Soc. Trans.* 19(4): 812-815 (1991).
Friedman et al. "Prolyl 4-hydroxylase is required for viability and morphogenesis in Caenorhabditis elegans", *Proc. Natl. Acad. Sci. USA*, 97:4736-4741 (2000).
Iliopoulus et al., Negative regulation of hypoxia-inducible genes by the von Hippel-Lindau protein :, *Proc. Natl. Acad. Sci. USA*, 93:10595-10599 (1996).
International Search Report and Written Opinion for PCT/US2007/061171 dated Jun. 4, 2007, 9 pages.
International Search Report and Written Opinion for PCT/US2014/012780 dated May 22, 2014, 11 pages.
Ivan, et al. "HIFα Targeted for VHL-Mediated Destruction by Proline Hydroxylation: Implications for O2 Sensing", *Science*, 292:464-468 (2001).
Jaakkola et al., "Targeting of HIF-alpha to the von Hippel-Lindau ubiquitylation complex by $O_2$ -regulated prolyl hydroxylation", *Science* 292 (5516):468-472 (2001).
Jiang et al., "Dimerization, DNA Binding, and Transactivation Properties of Hypoxia-inducible Factor 1*", *J. Biol. Chem.*, 271:17771-17778 (1996).
Kivirikko et al. "Prolyl 4-hydroxylase and their protein disulfide isomerase subunit", *Matrix Biol.*, 16:357-368 (1998).
Lando et al., "Oxygen-dependent regulation of hypoxia-inducible factors by prolyl and asparaginyl hydroxylation", *Eur.J. Biochem*, 270:781-790 (2003).
Majamaa et al. "Differences between collagen hydroxylases and 2-oxoglutarate dehydrogenase in their inhibition by structural analogues of 2-oxoglutarate", *Biochem J.*, 229:127-133 (1985).
Majamaa et al. "The 2-oxoglutarate binding site of prolyl 4-hyrdroxylase: Identification of distinct subsites and evidence for 2-oxoglutarate decarboxylation in a ligand reaction at the enzyme-bound ferrous ion", *Eur. J. Biochem.*, 138:239-245 (1984).
Maxwell et al., "The tumour suppressor protein VHL targets hypoxia-inducible factors for oxygen-dependent proteolysis", *Nature*, 399:271-275 (1999).
Richard et al., "Nonhypoxic Pathway Mediates the Induction of Hypoxia-inducible Factor 1α in Vascular Smooth Muscle Cells", *J. Biol. Chm*, 275:26765-26771 (2000).
Safran et al., "HIF hydroxylation and the mammalian oxygen-sensing pathway", *J. Clin. Invest.* 111(6):779-783 (2003).
Sandau et al., "Induction of Hypoxia-Inducible-Factor 1 by Nitric Oxide is Mediated via the PI 3K Pathway", *Biochem. Biophys. Res. Commun.*, 278:263-267(2000).
Sato et al., "Stability and Physicochemical Properties of Viracept Tablets", *Antibiotics and Chemotherapy* 14(9):1589-1592 (1998)—English Translation Not Available.
Sodhi et al., "MAPK and Akt Act Cooperatively but Independently on Hypoxia Inducible Factor-1α in rasV12 Unpregulation of VEGF", *Biochem.Biophys. Res.Commun.*, 287:292-300 (2001).
Sutter et al., "Hypoxia-inducible factor 1alpha protein expression is controlled by oxygen-regulated ubiquitination that is disrupted by deletions and missense mutations", *Proc. Natl. Acad. Sci. USA*, 97:4748-4753 (2000).
Tacchini, et al. "Hepatocyte growth factor signaling stimulates hypoxia inducible factor-1 (HIF-1) activity in HepG2 hepatoma cells", *Carcinogenesis*, 22:1363-1371 (2001).
Tanimoto et al., "Mechanism of regulation of the hypoxia-inducible factor-1alpha by the von Hippel-Lindau tumor suppressor protein", *EMBO J*, 19:4298-4309 (2000).
International Search Report and Written Opinion for PCT/US2014/012780 dated May 22, 2014, 13 pages.
Caira, "Crystalline Polymorphism of Organic Compounds," Topics in Current Chemistry, Jan. 1, 1998, pp. 163-208, vol. 198, Springer, Berlin, Germany.

* cited by examiner

CRYSTALLINE FORMS OF {[1-CYANO-5-(4-CHLOROPHENOXY)-4-HYDROXY-ISOQUINOLINE-3-CARBONYL]-AMINO}-ACETIC ACID

CROSS REFERENCE TO RELATED APPLICATIONS

This application is a U.S. national application filed under 37 C.F.R. §371(b) of International Application No. PCT/US2014/012780, filed on Jan. 23, 2014, which claims priority to U.S. Provisional Patent Application Ser. No. 61/756,361, filed on Jan. 24, 2013, the entire disclosures of which are hereby incorporated by reference.

BACKGROUND

Field

The present disclosure relates to crystalline forms of {[1-cyano-5-(4-chlorophenoxy)-4-hydroxy-isoquinoline-3-carbonyl]-amino}-acetic acid (Compound A), the process of preparing crystalline forms of Compound A, the pharmaceutical compositions containing them, and the methods of use thereof.

State of the Art

{[1-Cyano-5-(4-chlorophenoxy)-4-hydroxy-isoquinoline-3-carbonyl]-amino}-acetic acid (hereinafter, Compound A) is a potent inhibitor of hypoxia inducible factor (HIF) prolyl hydroxylase. HIF prolyl hydroxylase inhibitors are useful for increasing the stability and/or activity of HIF, and useful for treating and preventing disorders associated with HIF, including anemia, ischemia, and hypoxia. U.S. Pat. No. 7,928,120, which is incorporated herein in its entirety, describes a family of compounds that encompasses Compound A, including their structures, syntheses and methods of use.

A compound can exist in one or more crystalline forms. Crystalline forms of a drug substance can have different chemical and physical properties, including melting point, chemical reactivity, solubility, dissolution rate, optical and mechanical properties, vapor pressure, hygroscopicity, particle shape, density, flowability, and compatibility. These properties can have a direct effect on the ability to process and/or manufacture a compound as a drug product. Crystalline forms can also exhibit different stabilities and bioavailability. The most stable crystalline form of a drug product is often chosen during drug development based on the minimal potential for conversion to another crystalline form and on its greater chemical stability. To ensure the quality, safety, and efficacy of a drug product, it is important to choose a crystalline form that is stable, is manufactured reproducibly, and has favorable physicochemical properties. Therefore provided herein, are crystalline forms of Compound A, which can be manufactured as a drug product, and can be used to treat, and prevent HIF-associated disorders including conditions involving anemia, ischemia, and hypoxia.

SUMMARY

The present disclosure relates to crystalline forms of Compound A and methods for preparing crystalline forms.

One aspect of the present disclosure is directed to a crystalline form of {[1-cyano-5-(4-chlorophenoxy)-4-hydroxy-isoquinoline-3-carbonyl]-amino}-acetic acid (Compound A) having the following structure:

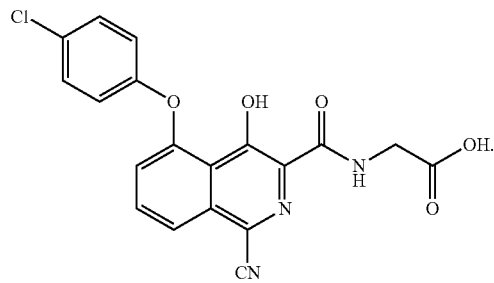

In one embodiment is provided crystalline Form 1 of {[1-cyano-5-(4-chlorophenoxy)-4-hydroxy-isoquinoline-3-carbonyl]-amino}-acetic acid (Compound A). In one embodiment, Compound A, Form 1 is characterized by having an X-ray powder diffractogram (XRPD) comprising at least one peak selected from 7.7, 11.2, 13.8, 14.7, 15.3, 15.8, 18.3, 21.1, and 22.2°2θ±0.2°2θ, as determined on a diffractogram using Cu—Kα radiation. In one embodiment, Form 1 is characterized by having an X-ray powder diffractogram comprising a peak at 18.3±0.2°2θ. In another embodiment, the diffractogram of Form 1 further comprises a peak at 11.2±0.2°2θ. In another embodiment, the diffractogram of Form 1 further comprises peaks at 7.7, 13.8, 21.1 and 22.2°2θ±0.2°2θ. In another embodiment, the diffractogram of Compound A, Form 1, is substantially as shown in FIG. 1.

In one embodiment, Compound A, Form 1 is characterized by a differential scanning calorimetry (DSC) curve that comprises an endotherm at about 251° C. In another embodiment, the DSC curve of Form 1 further comprises an exotherm at about 210° C. In another embodiment, the DSC curve of Compound A, Form 1 is substantially as shown in FIG. 2.

In one embodiment, Compound A, Form 1 is characterized by having an X-ray powder diffractogram comprising at least one peak selected from 7.7, 11.2, 13.8, 14.7, 15.3, 15.8, 18.3, 21.1, and 22.2°2θ±0.2°2θ, as determined on a diffractogram using Cu—Kα radiation; and by a differential scanning calorimetry (DSC) curve comprising an endotherm at about 251° C. In one embodiment, Form 1 is characterized by having an X-ray powder diffractogram comprising a peak at 18.3±0.2°2θ; and by a differential scanning calorimetry (DSC) curve comprising an endotherm at about 251° C. In another embodiment, the diffractogram of Form 1 further comprises peaks at 11.2, 7.7, 13.8, 21.1 and 22.2°2θ±0.2 °2θ; and the DSC curve of Form 1 further comprises an exotherm at about 210° C. In another embodiment, the diffractogram of Compound A, Form 1, is substantially as shown in FIG. 1; and the DSC curve of Compound A, Form 1 is substantially as shown in FIG. 2.

In one embodiment, the present disclosure provides crystalline Form 2 of {[1-cyano-5-(4-chlorophenoxy)-4-hydroxy-isoquinoline-3-carbonyl]-amino}-acetic acid (Compound A). In one embodiment, Compound A, Form 2 is characterized by having an X-ray powder diffractogram comprising at least one peak selected from 8.1, 10.6, 11.5, 14.5, 16.2, 19.3, 21.5, 21.9, 22.7, 24.5, and 26.6°2θ±0.2°2θ, as determined on a diffractogram using Cu—Kα radiation. In one embodiment, Form 2 is characterized by having an X-ray powder diffractogram comprising a peak at 19.3±0.2°2θ. In another embodiment, the diffractogram of Form 2 further comprises peaks at 10.6 and 11.5°2θ±0.2°2θ. In another embodiment, the diffractogram of Form 2 further comprises peaks at 14.5, 16.2, 24.5 and 26.6°2θ±0.2°2θ. In another embodiment, the diffractogram of Compound A, Form 2, is substantially as shown in FIG. 3.

In one embodiment, Compound A, Form 2 is characterized by a differential scanning calorimetry (DSC) curve that comprises an endotherm at about 249° C. In another embodiment, the DSC curve of Compound A, Form 2 is substantially as shown in FIG. 4.

In one embodiment, Compound A, Form 2 is characterized by having an X-ray powder diffractogram comprising at least one peak selected from 8.1, 10.6, 11.5, 14.5, 16.2, 19.3, 21.5, 21.9, 22.7, 24.5, and 26.6°2θ±0.2°2θ, as determined on a diffractogram using Cu—Kα radiation; and by a differential scanning calorimetry (DSC) curve comprising an endotherm at about 249° C. In one embodiment, Form 2 is characterized by having an X-ray powder diffractogram comprising a peak at 19.3±0.2°2θ; and by a DSC curve comprising an endotherm at about 249° C. In another embodiment, the diffractogram of Form 2 further comprises peaks at 10.6, 11.5, 14.5, 16.2, 24.5 and 26.6°2θ±0.2°2θ; and by a DSC curve comprising an endotherm at about 249° C. In another embodiment, the diffractogram of Compound A, Form 2, is substantially as shown in FIG. 3; and the DSC curve of Compound A, Form 2 is substantially as shown in FIG. 4.

In another aspect, the present disclosure is directed to a process for making crystalline Form 1 of {[1-cyano-5-(4-chlorophenoxy)-4-hydroxy-isoquinoline-3-carbonyl]-amino}-acetic acid (Compound A). In one embodiment, the process comprises:
  a) heating a mixture comprising a salt of {[1-cyano-5-(4-chlorophenoxy)-4-hydroxy-isoquinoline-3-carbonyl]-amino}-acetic acid (Compound A) optionally in the presence of a base;
  b) cooling the mixture; and
  c) adding an acid to the mixture.

In one embodiment, the process further comprises isolating Form 1 of Compound A.

In certain embodiments, the process for making crystalline Form 1 of {[1-cyano-5-(4-chlorophenoxy)-4-hydroxy-isoquinoline-3-carbonyl]-amino}-acetic acid (Compound A) comprises:
  a) heating a mixture comprising ethyl 1-cyano-5-(4-chlorophenoxy)-4-hydroxy-isoquinoline-3-carboxylate, glycine and sodium methoxide in methanol;
  b) cooling the mixture; and
  c) adding hydrochloric acid to the mixture.

In one embodiment, the process further comprises isolating Form 1 of Compound A.

In one embodiment, the process for making crystalline Form 1 of {[1-cyano-5-(4-chlorophenoxy)-4-hydroxy-isoquinoline-3-carbonyl]-amino}-acetic acid (Compound A) comprises heating Compound A in a suitable solvent. In one embodiment, the process further comprises isolating Form 1 of Compound A.

In another aspect, the present disclosure is directed to a process for making crystalline Form 2 of {[1-cyano-5-(4-chlorophenoxy)-4-hydroxy-isoquinoline-3-carbonyl]-amino}-acetic acid (Compound A). In one embodiment, the process comprises:
  a) heating a mixture comprising a salt of {[1-cyano-5-(4-chlorophenoxy)-4-hydroxy-isoquinoline-3-carbonyl]-amino}-acetic acid (Compound A);
  b) adding an acid to the mixture and continuing heating; and
  c) cooling the mixture.

In one embodiment, the process further comprises isolating Form 2 of Compound A.

In certain embodiments, the process for making crystalline Form 2 of {[1-cyano-5-(4-chlorophenoxy)-4-hydroxy-isoquinoline-3-carbonyl]-amino}-acetic acid (Compound A) comprises:
  a) heating a mixture comprising the sodium salt of {[1-cyano-5-(4-chlorophenoxy)-4-hydroxy-isoquinoline-3-carbonyl]-amino}-acetic acid (Compound A) in water to about 80-85° C.;
  b) adding acetic acid to the mixture and continuing heating at about 80-85° C.; and
  c) cooling the mixture.

In one embodiment, the process further comprises isolating Form 2 of Compound A.

In one embodiment, the process for making crystalline Form 2 of {[1-cyano-5-(4-chlorophenoxy)-4-hydroxy-isoquinoline-3-carbonyl]-amino}-acetic acid (Compound A) comprises heating Compound A in a suitable solvent. In one embodiment, the process further comprises isolating Form 2 of Compound A.

In one embodiment, the process for making crystalline Form 2 of {[1-cyano-5-(4-chlorophenoxy)-4-hydroxy-isoquinoline-3-carbonyl]-amino}-acetic acid (Compound A), comprises heating Form 1 of Compound A.

In one embodiment, the process further comprises isolating Form 2 of Compound A.

In another aspect, the present disclosure is directed to a pharmaceutical composition comprising one or more crystalline forms of {[1-cyano-5-(4-chlorophenoxy)-4-hydroxy-isoquinoline-3-carbonyl]-amino}-acetic acid (Compound A) having the following structure:

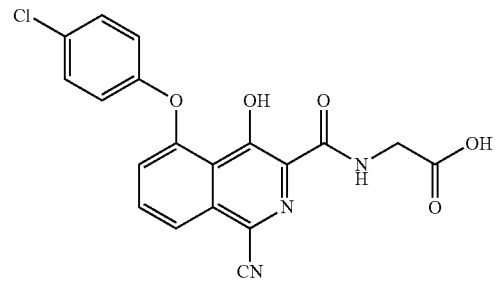

and at least one pharmaceutically acceptable excipient.

In one embodiment, the pharmaceutical composition comprises Compound A, Form 1, and at least one pharmaceutically acceptable excipient. In another embodiment, the pharmaceutical composition comprises Compound A, at least 90% of which is present as Form 1, and at least one pharmaceutically acceptable excipient. In yet another embodiment, the pharmaceutical composition comprises Compound A, at least 95%, 98%, 99%, 99.5%, 99.8%, 99.9%, 99.95%, 99.98% or 99.99% of which is present as Form 1, and at least one pharmaceutically acceptable excipient. In another embodiment, the pharmaceutical composition comprises Compound A, at least 90% to 99.99% of which is present as Form 1, and at least one pharmaceutically acceptable excipient.

In one embodiment, the pharmaceutical composition comprises Compound A, Form 2, and at least one pharmaceutically acceptable excipient. In another embodiment, the pharmaceutical composition comprises Compound A, at least 90% of which is present as Form 2, and at least one pharmaceutically acceptable excipient. In yet another embodiment, the pharmaceutical composition comprises Compound A, at least 95%, 98%, 99%, 99.5%, 99.8%, 99.9%, 99.95%, 99.98% or 99.99% of which is present as Form 2, and at least one pharmaceutically acceptable excipient. In another embodiment, the pharmaceutical composition comprises Compound A, at least 90% to 99.99% of which is present as Form 2, and at least one pharmaceutically acceptable excipient. In one embodiment, the pharmaceutical composition comprises Compound A, no more than 10%, 5%, 2%, 1%, 0.5%, 0.2%, 0.1%, 0.05%, 0.02% or 0.01% of which is present as Form 1, and at least one pharmaceutically acceptable excipient. In one embodiment, the pharmaceutical composition comprises Compound A, no more than 0.1% to 10% of which is present as Form 1, and at least one pharmaceutically acceptable excipient.

In one embodiment, the pharmaceutical composition further comprises an additional therapeutic agent selected from the group consisting of vitamin B12, folic acid, ferrous sulfate, recombinant human erythropoietin, and an erythropoiesis stimulating agent (ESA). In another embodiment, the pharmaceutical composition is formulated for oral delivery. In another embodiment, the pharmaceutical composition is formulated as a tablet or a capsule.

In another aspect, the present disclosure is directed to a method of treating, pretreating, or delaying onset of a condition associated with or mediated at least in part by hypoxia inducible factor (HIF), the method comprising administering to a patient a therapeutically effective amount of a pharmaceutical composition comprising one or more crystalline forms of Compound A. In one embodiment, the condition associated with or mediated at least in part by HIF is tissue damage associated with ischemia or hypoxia. In another embodiment, the ischemia is associated with an ischemic event selected from the group consisting of myocardial infarction, pulmonary embolism, intestinal infarction, chronic kidney failure, ischemic stroke, renal ischemic-reperfusion injury, cardiac cirrhosis, transient ischemic attack, macular degeneration, peripheral artery disease, and congestive heart failure. In one embodiment of this method, the pharmaceutical composition comprises Compound A, Form 1. In one embodiment of this method, the pharmaceutical composition comprises Compound A, Form 2.

In another aspect, the present disclosure is directed to a method of treating, pretreating, or delaying onset of a condition associated with or mediated at least in part by erythropoietin (EPO), the method comprising administering to a patient a therapeutically effective amount of a pharmaceutical composition comprising one or more crystalline forms of Compound A. In one embodiment of this method, the pharmaceutical composition comprises Compound A, Form 1. In one embodiment of this method, the pharmaceutical composition comprises Compound A, Form 2.

In another aspect, the present disclosure is directed to a method of treating, pretreating, or delaying onset of anemia, the method comprising administering to a patient a therapeutically effective amount of a pharmaceutical composition comprising one or more crystalline forms of Compound A. In one embodiment, the anemia is associated with a chronic disease or a condition selected from the group consisting of diabetes, cancer, ulcers, kidney disease, immunosuppressive disease, infection, and inflammation. In another embodiment, the anemia is associated with a procedure or treatment selected from the group consisting of radiation therapy, chemotherapy, dialysis, and surgery. In another embodiment, the anemia is associated with blood loss caused by bleeding disorders, trauma, injury, surgery, etc. In yet another embodiment, the anemia is associated with abnormal hemoglobin, abnormal erythrocytes, or defects in iron transport, processing, or utilization. In one embodiment of this method, the pharmaceutical composition comprises Compound A, Form 1. In one embodiment of this method, the pharmaceutical composition comprises Compound A, Form 2.

DETAILED DESCRIPTION

Figure 1:
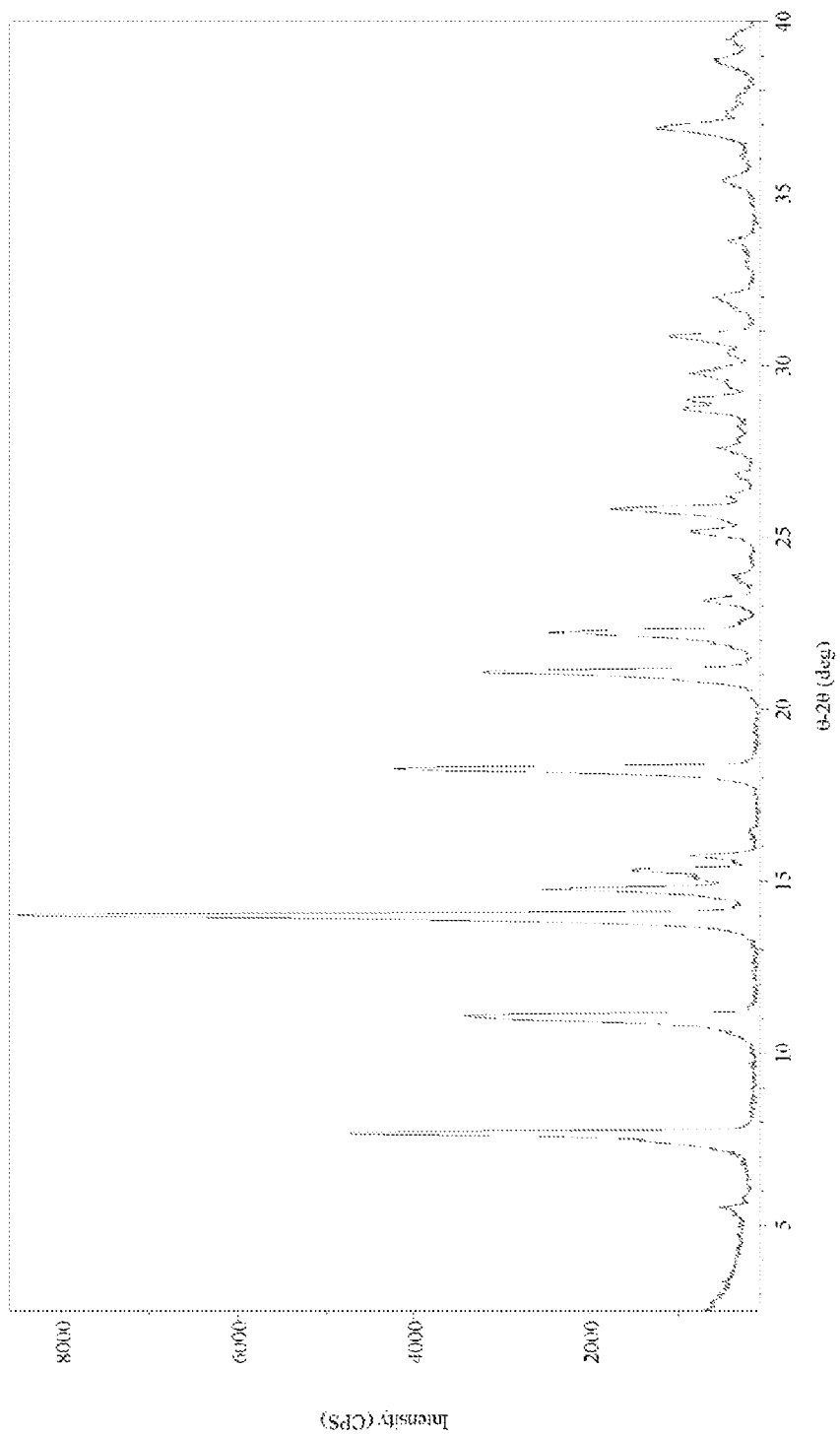
FIG. 1 is an XRPD pattern of crystalline Form 1, Compound A.

As noted above, this disclosure is directed, in part, to the crystalline forms of {[1-cyano-5-(4-chlorophenoxy)-4-hydroxy-isoquinoline-3-carbonyl]-amino}-acetic acid (Compound A) having the following structure:

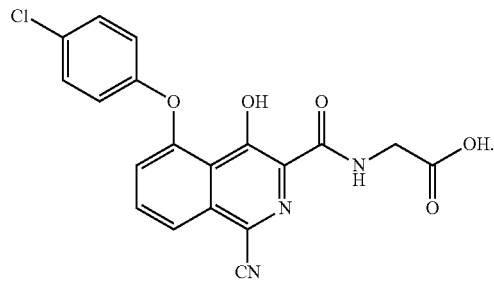

Prior to discussing in further detail, the following terms will be defined.

1. Definitions

As used herein, the following terms have the following meanings.

The singular forms "a," "an," and "the" and the like include plural referents unless the context clearly dictates otherwise. Thus, for example, reference to "a compound" includes both a single compound and a plurality of different compounds.

The term "about" when used before a numerical designation, e.g., temperature, time, amount, and concentration, including a range, indicates approximations which may vary by ±10%, ±5% or ±1%.

"Administration" refers to introducing an agent into a patient. A therapeutic amount can be administered, which can be determined by the treating physician or the like. An oral route of administration is preferred for the crystalline forms of Compound A described herein. The related terms and phrases "administering" and "administration of", when used in connection with a compound or pharmaceutical composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer a drug and/or provides a patient with a prescription for a drug is administering the drug to the patient. In any event, administration entails delivery of the drug to the patient.

"Characterization" refers to obtaining data which may be used to identify and distinguish a solid form of a compound, for example, to identify whether the solid form is amorphous or crystalline and whether it is unsolvated or solvated. The process by which solid forms are characterized involves analyzing data collected on the polymorphic forms so as to allow one of ordinary skill in the art to distinguish one solid form from other solid forms containing the same material. Chemical identity of solid forms can often be determined with solution-state techniques such as $^{13}$C NMR or $^{1}$H NMR. While these may help identify a material, and a solvent molecule for a solvate, such solution-state techniques themselves may not provide information about the solid state. There are, however, solid-state analytical techniques that can be used to provide information about solid-state structure and differentiate among polymorphic solid forms, such as single crystal X-ray diffraction, X-ray powder diffraction (XRPD), solid state nuclear magnetic resonance (SS-NMR), and infrared and Raman spectroscopy, and thermal techniques such as differential scanning calorimetry (DSC), thermogravimetry (TG), melting point, and hot stage microscopy.

To "characterize" a solid form of a compound, one may, for example, collect XRPD data on solid forms of the compound and compare the XRPD peaks of the forms. For example, when only two solid forms, 1 and 2, are compared and the form 1 pattern shows a peak at an angle where no peaks appear in the form 2 pattern, then that peak, for that compound, distinguishes form 1 from form 2 and further acts to characterize form 1. The collection of peaks which distinguish form 1 from the other known forms is a collection of peaks which may be used to characterize form 1. Those of ordinary skill in the art will recognize that there are often multiple ways, including multiple ways using the same analytical technique, to characterize solid forms. Additional peaks could also be used, but are not necessary, to characterize the form up to and including an entire diffraction pattern. Although all the peaks within an entire XRPD pattern may be used to characterize such a form, a subset of that data may, and typically is, used to characterize the form.

The "crystalline form" of Compound A is a crystalline solid form of Compound A, e.g., Form 1 or Form 2. The Form 1 or Form 2 crystal lattice is substantially free of solvents of crystallization. However, any solvent present is not included in the crystal lattice and is randomly distributed outside the crystal lattice. Therefore, Form 1 or Form 2 crystals in bulk may contain, outside the crystal lattice, small amounts of one or more solvents, such as the solvents used in its synthesis or crystallization. As used above, "substantially free of" and "small amounts," refers to the presence of solvents preferably less than 10,000 parts per million (ppm), or more preferably, less than 500 ppm.

"Excipient" as used herein means an inert or inactive substance used in the production of pharmaceutical products, including without limitation any substance used as a binder, disintegrant, coating, compression/encapsulation aid, cream or lotion, lubricant, parenteral, sweetener or flavoring, suspending/gelling agent, or wet granulation agent. Binders include, e.g., carbopol, povidone, xanthan gum, etc.; coatings include, e.g., cellulose acetate phthalate, ethylcellulose, gellan gum, maltodextrin, etc.; compression/encapsulation aids include, e.g., calcium carbonate, dextrose, fructose dc, honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams and lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; parenterals include, e.g., mannitol, povidone, etc.; plasticizers include, e.g., dibutyl sebacate, polyvinylacetate phthalate, etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Maturation" or "maturating" refers to incubation of a mixture of a solid material in a particular solvent, subjected to heat/cool cycles for a particular period of time. For example, maturation was carried out at room temperature for 4 h followed by incubation at 50° C. for another 4 h (incubated at 50° C./room temperature (4 h-cycles)), for a period of 16 to 24 h.

"Room temperature" refers to (22±5° C.

"Therapeutically effective amount" or "therapeutic amount" refers to an amount of a drug or an agent that when administered to a patient suffering from a condition, will have the intended therapeutic effect, e.g., alleviation, amelioration, palliation or elimination of one or more manifestations of the condition in the patient. The therapeutically effective amount will vary depending upon the subject and the condition being treated, the weight and age of the subject, the severity of the condition, the particular composition or excipient chosen, the dosing regimen to be followed, timing of administration, the manner of administration and the like, all of which can be determined readily by one of ordinary skill in the art. The full therapeutic effect does not necessarily occur by administration of one dose, and may occur only after administration of a series of doses. Thus, a therapeutically effective amount may be administered in one or more administrations. For example, and without limitation, a therapeutically effective amount of an agent, in the context of treating anemia, refers to an amount of the agent that alleviates, ameliorates, palliates, or eliminates one or more symptoms of anemia in the patient.

"Treatment", "treating", and "treat" are defined as acting upon a disease, disorder, or condition with an agent to reduce or ameliorate the harmful or any other undesired effects of the disease, disorder, or condition and/or its symptoms. Treatment, as used herein, covers the treatment of a human patient, and includes: (a) reducing the risk of occurrence of the condition in a patient determined to be predisposed to the disease but not yet diagnosed as having the condition, (b) impeding the development of the condition, and/or (c) relieving the condition, i.e., causing regression of the condition and/or relieving one or more symptoms of the condition.

An "XRPD pattern" is an x-y graph with diffraction angle (typically ° 2θ) on the x-axis and intensity on the y-axis. The peaks within this pattern may be used to characterize a crystalline solid form. As with any data measurement, there is variability in XRPD data. The data are often represented solely by the diffraction angle of the peaks rather than including the intensity of the peaks because peak intensity can be particularly sensitive to sample preparation (for example, particle size, moisture content, solvent content, and preferred orientation effects influence the sensitivity), so samples of the same material prepared under different conditions may yield slightly different patterns; this variability is usually greater than the variability in diffraction angles. Diffraction angle variability may also be sensitive to sample preparation. Other sources of variability come from instrument parameters and processing of the raw X-ray data: different X-ray instruments operate using different parameters and these may lead to slightly different XRPD patterns from the same solid form, and similarly different software packages process X-ray data differently and this also leads to variability. These and other sources of variability are known to those of ordinary skill in the pharmaceutical arts. Due to such sources of variability, it is usual to assign a variability of ±0.2°2θ to diffraction angles in XRPD patterns.

2. Preparation of Crystalline Forms of Compound A

In one aspect, the present disclosure is directed to a process for making crystalline Form 1 of {[1-cyano-5-(4-chlorophenoxy)-4-hydroxy-isoquinoline-3-carbonyl]-amino}-acetic acid (Compound A). In one embodiment, the process comprises:
a) heating a mixture comprising a salt of {[1-cyano-5-(4-chlorophenoxy)-4-hydroxy-isoquinoline-3-carbonyl]-amino}-acetic acid (Compound A) optionally in the presence of a base;
b) cooling the mixture; and
c) adding an acid to the mixture.

Typically for this process, the base, if added, is in excess to the salt. For example, for 1 equivalent of salt, about 2 to about 20 equivalents of base, about 5 to about 15 equivalents of base, about 10 to about 15 equivalents of base, or about 10, about 11, about 12, about 13, about 14 or about 15 equivalents of base is added. Typically for this process, the heating is carried out at about 60° C. to about 85° C., at about 65° C. to about 82° C., or at about 65° C., about 80° C. or about 82° C., until the reaction is complete as determined by LC-MS. Typically, the acid is added to bring the mixture to a pH of about 1 to about 4, to a pH of about 2 to about 3, or to a pH of about 3.

In one embodiment, the process further comprises isolating Form 1 of Compound A.

In one embodiment, the salt of {[1-cyano-5-(4-chlorophenoxy)-4-hydroxy-isoquinoline-3-carbonyl]-amino}-acetic acid (Compound A) is provided by mixing ethyl 1-cyano-5-(4-chlorophenoxy)-4-hydroxy-isoquinoline-3-carboxylate, glycine and a base. Typically for this process, for 1 equivalent of ethyl 1-cyano-5-(4-chlorophenoxy)-4-hydroxy-isoquinoline-3-carboxylate, about 15 to about 25 equivalents of glycine and about 10 to about 20 equivalents of base, or about 20 equivalents of glycine and about 15 equivalents of base is added.

In one embodiment, the base is sodium methoxide.
In one embodiment, the acid is hydrochloric acid.
In one embodiment, the process is performed in methanol.
In another embodiment, the process for making crystalline Form 1 of Compound A comprises:
a) heating a mixture comprising ethyl 1-cyano-5-(4-chlorophenoxy)-4-hydroxy-isoquinoline-3-carboxylate, glycine and sodium methoxide in methanol;
b) cooling the mixture;
c) adding hydrochloric acid to the mixture; and
d) isolating Form 1 of Compound A.

Typically for this process, for 1 equivalent of ethyl 1-cyano-5-(4-chlorophenoxy)-4-hydroxy-isoquinoline-3-carboxylate, about 15 to about 25 equivalents of glycine and about 10 to about 20 equivalents of sodium methoxide, or about 20 equivalents of glycine and about 15 equivalents of sodium methoxide is added. Typically for this process, the heating is carried out at reflux until the reaction is complete as determined by LC-MS. Typically, the acid is added to bring the mixture to a pH of about 1 to about 4, to a pH of about 2 to about 3, or to a pH of about 3.

In one embodiment, the present disclosure provides for a process for making crystalline Form 1 of {[1-cyano-5-(4-chlorophenoxy)-4-hydroxy-isoquinoline-3-carbonyl]-amino}-acetic acid (Compound A), comprising heating Compound A in a suitable solvent. In one embodiment, the process further comprises isolating Form 1 of Compound A.

In one embodiment, the suitable solvent is acetonitrile and the heating is at reflux (usually about 81-82° C.). Typically, the heating is carried out until a clear solution forms. Typically, the solution is cooled to about room temperature and then to a low temperature, for example, about 5° C.

In one embodiment, the suitable solvent is neat acetic acid and the heating is at about 80° C.

In another embodiment, the process for making crystalline Form 1 of Compound A comprises:
a) heating Compound A in acetonitrile at reflux;
b) cooling the mixture; and
c) isolating Form 1 of Compound A.

Typically the cooling is to about room temperature.
In another embodiment, the process for making crystalline Form 1 of Compound A comprises:
a) heating Compound A in neat acetic acid at about 80° C.;
b) cooling the mixture; and
c) isolating Form 1 of Compound A.

Typically the cooling is to about room temperature.
In one embodiment, the present disclosure provides for a process for making crystalline Form 1 of {[1-cyano-5-(4-chlorophenoxy)-4-hydroxy-isoquinoline-3-carbonyl]-amino}-acetic acid (Compound A), comprising heating XRPD 3 or XRPD 4 of Compound A to a temperature of greater than about 40° C.

In the above embodiments, the isolating step may comprise one or more of the following: cooling the mixture, stirring the mixture, filtering, washing, and drying the solid in a vacuum oven to constant weight.

In another aspect, the present disclosure is directed to a process for making crystalline Form 2 of {[1-cyano-5-(4-chlorophenoxy)-4-hydroxy-isoquinoline-3-carbonyl]-amino}-acetic acid (Compound A). In one embodiment, the process comprises:
a) heating a mixture comprising a salt of {[1-cyano-5-(4-chlorophenoxy)-4-hydroxy-isoquinoline-3-carbonyl]-amino}-acetic acid (Compound A);

b) adding an acid to the mixture and continuing heating; and c) cooling the mixture.

Typically, about 3 to about 6 equivalents, or about 5 equivalents of the acid is added. Typically, the heating is to about 80° C. Typically, the cooling is to about room temperature.

In one embodiment, the process further comprises isolating Form 2 of Compound A.

In one embodiment, the salt of Compound A is provided by mixing Compound A with a base. Typically, about 1 to 1.5 equivalents or about 1.25 equivalents of the base is used.

In one embodiment, the base is sodium hydroxide.

In one embodiment, the process is performed in water.

In one embodiment, the heating is a temperature of greater than about 80° C. In certain embodiments, the heating is a temperature of about 80-85° C.

In one embodiment, the acid is acetic acid.

In one embodiment, the salt of Compound A is provided by mixing ethyl 1-cyano-5-(4-chlorophenoxy)-4-hydroxy-isoquinoline-3-carboxylate, glycine and a base.

In one embodiment, the base is sodium methoxide.

In another embodiment, the present disclosure provides for a process for making crystalline Form 2 of {[1-cyano-5-(4-chlorophenoxy)-4-hydroxy-isoquinoline-3-carbonyl]-amino}-acetic acid (Compound A) comprising:
  a) heating a mixture comprising the sodium salt of {[1-cyano-5-(4-chlorophenoxy)-4-hydroxy-isoquinoline-3-carbonyl]-amino}-acetic acid (Compound A) in water to about 80-85° C.;
  b) adding acetic acid to the mixture and continuing heating at about 80-85° C.;
  c) cooling the mixture; and
  d) isolating Form 2 of Compound A.

In one embodiment, the sodium salt of Compound A is provided by mixing Compound A with sodium hydroxide. Typically, about 1 to 1.5 equivalents or about 1.25 equivalents of sodium hydroxide is added to Compound A.

In one embodiment, the process for making crystalline Form 2 of Compound A comprises:
  a) heating a mixture comprising Compound A and sodium hydroxide in water to about 80-85° C.;
  b) adding acetic acid to the mixture and continuing heating at about 80-85° C.;
  c) cooling the mixture; and
  d) isolating Form 2 of Compound A.

In another embodiment, the present disclosure provides for a process for making crystalline Form 2 of {[1-cyano-5-(4-chlorophenoxy)-4-hydroxy-isoquinoline-3-carbonyl]-amino}-acetic acid (Compound A) comprising heating Compound A in a suitable solvent. In one embodiment, the process further comprises isolating Form 2 of Compound A.

In one embodiment, the suitable solvent is isopropyl acetate and the heating is at reflux. Typically, in this embodiment, the heating is carried out from 1 hour to overnight.

In one embodiment, the suitable solvent is water and the heating is at about 80° C. Typically, in this embodiment, the heating is carried out from 1 hour to overnight.

In one embodiment, the process for making crystalline Form 2 of Compound A comprises:
  a) heating Compound A in isopropyl acetate to reflux; and
  b) isolating Form 2 of Compound A.

In another embodiment, the process for making crystalline Form 2 of Compound A comprises:
  a) heating Compound A in water at about 80° C.;
  b) isolating Form 2 of Compound A.

In another embodiment, the process for making crystalline Form 2 of Compound A comprises maturating Compound A, Form 1 at an elevated temperature (e.g., at about 50° C.), and at certain relative humidity (RH) (e.g., at about 75% RH), whereby Compound A, Form 2 is formed. In one embodiment, the process further comprises isolating Form 2 of Compound A.

In another embodiment, the process for making crystalline Form 2 of Compound A comprises heating crystalline Form 1 of Compound A, whereby Compound A, Form 2 is formed. In one embodiment, the heating comprises a temperature of about 200° C. In one embodiment, the process further comprises isolating Form 2 of Compound A.

In another embodiment, the process for making crystalline Form 2 of Compound A comprises heating XRPD 5, XRPD 6 or XRPD 7 of Compound A of to a temperature of greater than about 40° C.

In the above embodiments, the isolating step may comprise one or more of the following: cooling the mixture, stirring the mixture, filtering, washing, and drying the solid in a vacuum oven to constant weight.

3. Characterization of Crystalline Forms of Compound A

The crystalline form of {[1-cyano-5-(4-chlorophenoxy)-4-hydroxy-isoquinoline-3-carbonyl]-amino}-acetic acid (Compound A) is characterized by a variety of methods as discussed below.

X-Ray Powder Diffraction (XRPD)

In one embodiment, Compound A, Form 1 is characterized by having an X-ray powder diffractogram comprising at least one peak selected from 7.7, 11.2, 13.8, 14.7, 15.3, 15.8, 18.3, 21.1, and 22.2°2θ±0.2°2θ, as determined on a diffractogram using Cu—Kα radiation. In one embodiment, Form 1 is characterized by having an X-ray powder diffractogram comprising a peak at 18.3±0.2°2θ. In another embodiment, the diffractogram of Form 1 further comprises a peak at 11.2±0.2°2θ. In another embodiment, the diffractogram of Form 1 further comprises peaks at 7.7, 13.8, 21.1 and 22.2°2θ±0.2°2θ. In another embodiment, the diffractogram of Compound A, Form 1, is substantially as shown in FIG. 1.

Figure 3:
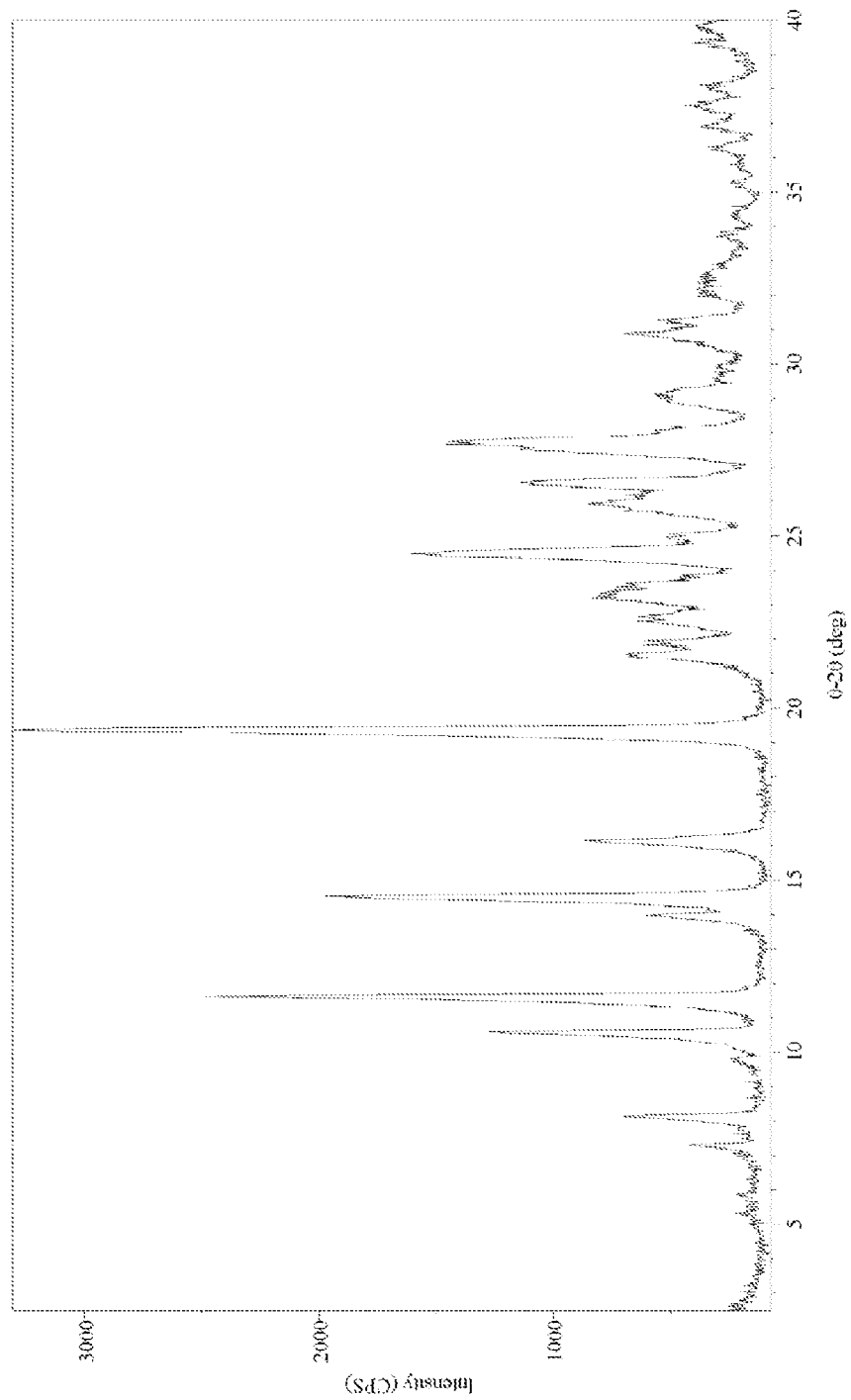
FIG. 3 is an XRPD pattern of crystalline Form 2, Compound A.

In one embodiment, Compound A, Form 2 is characterized by having an X-ray powder diffractogram comprising at least one peak selected from 8.1, 10.6, 11.5, 14.5, 16.2, 19.3, 21.5, 21.9, 22.7, 24.5, and 26.6°2θ±0.2°2θ, as determined on a diffractogram using Cu—Kα radiation. In one embodiment, Form 2 is characterized by having an X-ray powder diffractogram comprising a peak at 19.3±0.2°2θ. In another embodiment, the diffractogram of Form 2 further comprises peaks at 10.6 and 11.5°2θ±0.2°2θ. In another embodiment, the diffractogram of Form 2 further comprises peaks at 14.5, 16.2, 24.5 and 26.6°2θ±0.2°2θ. In another embodiment, the diffractogram of Compound A, Form 2, is substantially as shown in FIG. 3.

Differential Scanning Calorimetry (DSC)

Figure 2:
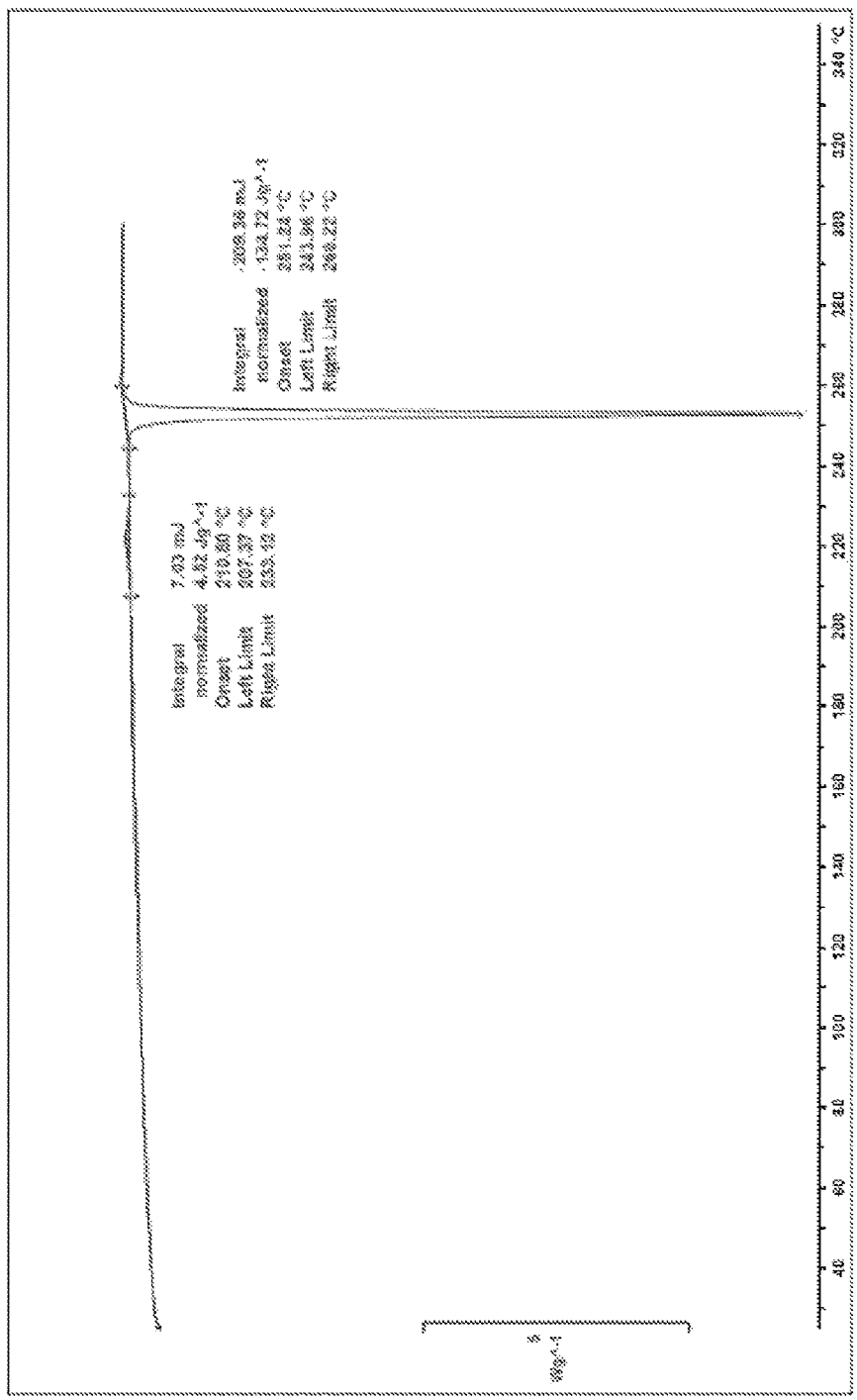
FIG. 2 is a DSC pattern of crystalline Form 1, Compound A.

In one embodiment, Compound A, Form 1 is characterized by a differential scanning calorimetry (DSC) curve that comprises an endotherm at about 251° C. In another embodiment, DSC curve of Form 1 further comprises an exotherm at about 210° C. In another embodiment, the DSC curve of Compound A, Form 1 is substantially as shown in FIG. 2.

Figure 4:
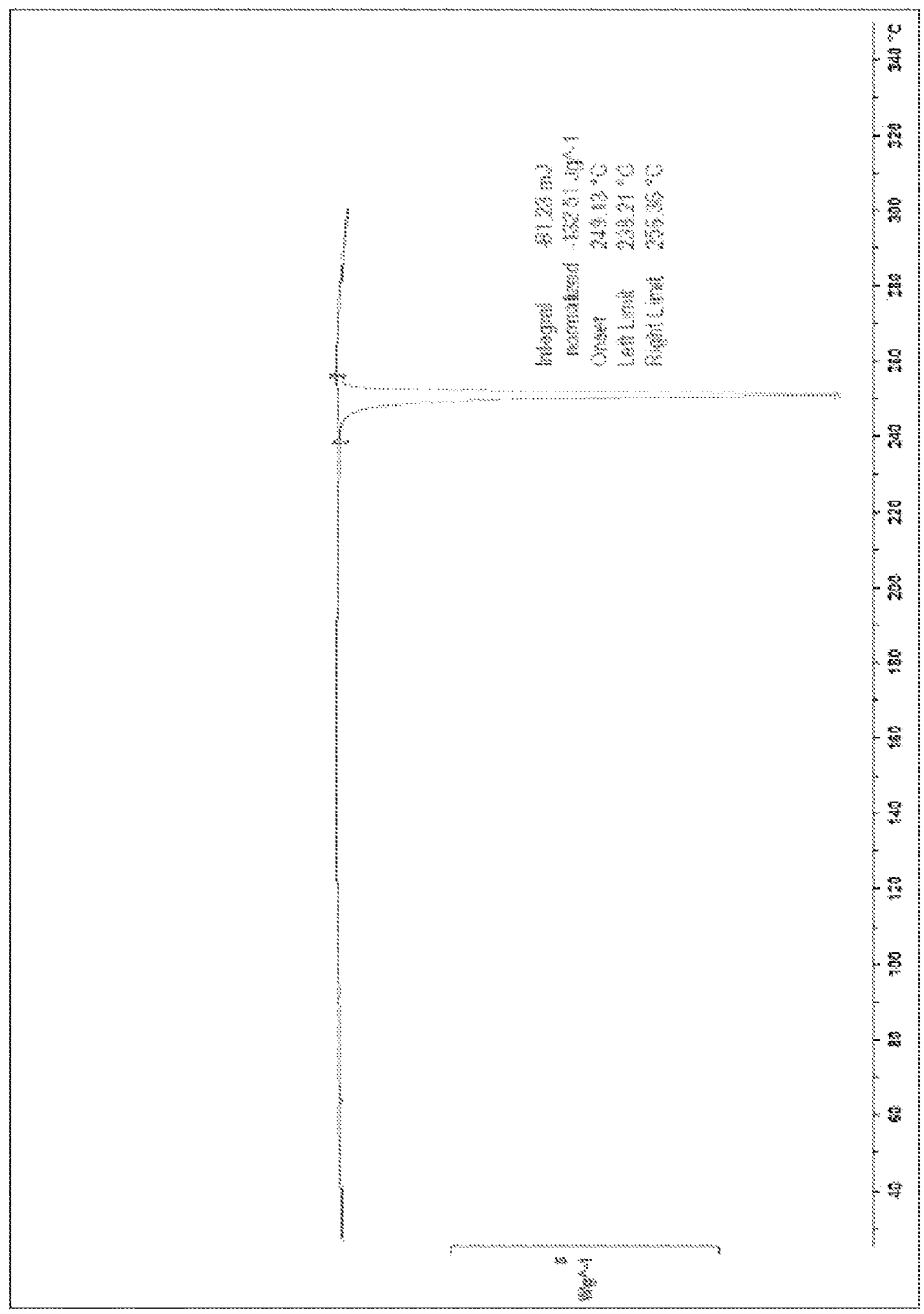
FIG. 4 is a DSC pattern of crystalline Form 2, Compound A.

In one embodiment, Compound A, Form 2 is characterized by a differential scanning calorimetry (DSC) curve that comprises an endotherm at about 249° C. In another embodiment, the DSC curve of Compound A, Form 2 is substantially as shown in FIG. 4.

In one embodiment, Compound A, Form 1 is characterized by having an X-ray powder diffractogram comprising at least one peak selected from 7.7, 11.2, 13.8, 14.7, 15.3, 15.8, 18.3, 21.1, and 22.2°2θ±0.2°2θ, as determined on a diffractogram using Cu—Kα radiation; and by a differential scanning calorimetry (DSC) curve comprising an endotherm at about 251° C. In one embodiment, Form 1 is characterized by having an X-ray powder diffractogram comprising a peak at 18.3±0.2°2θ; and by a differential scanning calorimetry (DSC) curve comprising an endotherm at about 251° C. In another embodiment, the diffractogram of Form 1 further comprises peaks at 11.2, 7.7, 13.8, 21.1 and 22.2°2θ±0.2 °2θ; and the DSC curve of Form 1 further comprises an exotherm at about 210° C. In another embodiment, the diffractogram of Compound A, Form 1, is substantially as shown in FIG. 1; and the DSC curve of Compound A, Form 1 is substantially as shown in FIG. 2.

In one embodiment, Compound A, Form 2 is characterized by having an X-ray powder diffractogram comprising at least one peak selected from 8.1, 10.6, 11.5, 14.5, 16.2, 19.3, 21.5, 21.9, 22.7, 24.5, and 26.6°2θ±0.2°2θ, as determined on a diffractogram using Cu—Kα radiation; and by a differential scanning calorimetry (DSC) curve comprising an endotherm at about 249° C. In one embodiment, Form 2 is characterized by having an X-ray powder diffractogram comprising a peak at 19.3±0.2°2θ; and by a DSC curve comprising an endotherm at about 249° C. In another embodiment, the diffractogram of Form 2 further comprises peaks at 10.6, 11.5, 14.5, 16.2, 24.5 and 26.6°2θ±0.2°2θ; and by a DSC curve comprising an endotherm at about 249° C. In another embodiment, the diffractogram of Compound A, Form 2, is substantially as shown in FIG. 3; and the DSC curve of Compound A is substantially as shown in FIG. 4.

Thermo Gravimetric Analysis (TGA)

In one embodiment, thermo gravimetric analysis of Compound A, Form 1, shows no weight loss until degradation starting at about 260° C.

In one embodiment, thermo gravimetric analysis of Compound A, Form 2, shows no weight loss until degradation starting at about 260° C.

4. Stability of Crystalline Forms of Compound A

The relative stability of Form 1 and Form 2 have been studied under different conditions (see Example 3). Both Form 1 and Form 2 are stable to humidity and to temperature up to at least ~200° C. and both forms exhibit low hygroscopicity.

A number of experiments (see Example 3) show that Form 1 converts to Form 2 under various conditions: heating above 200° C.; maturation in isopropyl acetate (IPAc) at 5° C., 25° C. and 50° C.; maturation in water at 50° C./room temperature; and by reflux in water. The transformation of Form 2 into Form 1 has not been observed. Form 1, however, remains unchanged in water at 25° C. after six days.

Therefore, Form 2 is thermodynamically more stable than Form 1 under the conditions investigated and thus, Form 2 may provide advantages in manufacturing and formulating Compound A.

5. Other Solvates of Compound A

The disclosure also provides solvates of Compound A. Maturation of Compound A, Form 1 in different solvents results in several solvates of Compound A (see Example 4). These solvates are characterized by XRPD and named after their XRPD patterns:

XRPD 3 and XRPD 4, a group of iso-structural solvates from toluene, n-heptane, tetrahydrofuran (THF), ethyl acetate (EtOAc), iso-propyl alcohol (IPA), ethanol (EtOH), nitromethane or EtOH-water;

XRPD 5, dimethylformamide (DMF) solvate;

XRPD 6, n-methyl pyrrolidone (NMP) solvate; and

XRPD 7—1,4-dioxane solvate.

¹H NMR analyses, DSC and TGA thermal analyses confirm that these solids are solvates rather than polymorphs (see Example 4).

6. Pharmaceutical Compositions, Formulations and Routes of Administration

In one aspect, the present disclosure is directed to a pharmaceutical composition comprising one or more crystalline form of {[1-cyano-5-(4-chlorophenoxy)-4-hydroxy-isoquinoline-3-carbonyl]-amino}-acetic acid (Compound A) having the following structure:

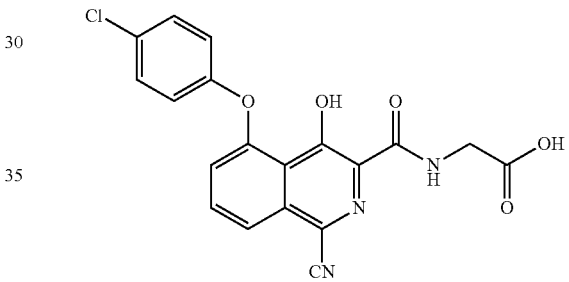

and at least one pharmaceutically acceptable excipient.

In one embodiment, the pharmaceutical composition comprises Compound A, Form 1, and at least one pharmaceutically acceptable excipient. In another embodiment, the pharmaceutical composition comprises Compound A, at least 90% of which is present as Form 1, and at least one pharmaceutically acceptable excipient. In yet another embodiment, the pharmaceutical composition comprises Compound A, at least 95%, 98%, 99%, 99.5%, 99.8%, 99.9%, 99.95%, 99.98% or 99.99% of which is present as Form 1, and at least one pharmaceutically acceptable excipient.

In one embodiment, the pharmaceutical composition comprises Compound A, Form 2, and at least one pharmaceutically acceptable excipient. In another embodiment, the pharmaceutical composition comprises Compound A, at least 90% of which is present as Form 2, and at least one pharmaceutically acceptable excipient. In yet another embodiment, the pharmaceutical composition comprises Compound A, at least 95%, 98%, 99%, 99.5%, 99.8%, 99.9%, 99.95%, 99.98% or 99.99% of which is present as Form 2, and at least one pharmaceutically acceptable excipient. In one embodiment, the pharmaceutical composition comprises Compound A, no more than 10%, 5%, 2%, 1%, 0.5%, 0.2%, 0.1%, 0.05%, 0.02% or 0.01% of which is present as Form 1, and at least one pharmaceutically acceptable excipient.

In one embodiment, the pharmaceutical composition further comprises an additional therapeutic agent selected from the group consisting of vitamin B12, folic acid, ferrous sulfate, recombinant human erythropoietin, and an erythropoiesis stimulating agent (ESA). In another embodiment, the pharmaceutical composition is formulated for oral delivery. In another embodiment, the pharmaceutical composition is formulated as a tablet or a capsule.

The crystalline forms of the present disclosure can be delivered directly or in pharmaceutical compositions along with suitable excipients, as is well known in the art. Various treatments embodied herein can comprise administration of an effective amount of a crystalline form of the disclosure to a subject in need, e.g., a subject having or at risk for anemia due to, e.g., chronic renal failure, diabetes, cancer, AIDS, radiation therapy, chemotherapy, kidney dialysis, or surgery. In one embodiment, the subject is a mammalian subject, and in one embodiment, the subject is a human subject.

An effective amount of a crystalline form can readily be determined by routine experimentation, as can the most effective and convenient route of administration and the most appropriate formulation. In one embodiment, the dosage may be from 0.1 mg/kg to about 700 mg/kg per day. Various formulations and drug delivery systems are available in the art. See, e.g., Gennaro, A. R., ed. (1995) *Remington's Pharmaceutical Sciences*, supra.

Suitable routes of administration may, for example, include oral, rectal, transmucosal, nasal, or intestinal administration and parenteral delivery, including intramuscular, subcutaneous, intramedullary injections, as well as intrathecal, direct intraventricular, intravenous, intraperitoneal, intranasal, or intraocular injections. The crystalline form or composition thereof may be administered in a local rather than a systemic manner. For example, a crystalline form or composition thereof can be delivered via injection or in a targeted drug delivery system, such as a depot or sustained release formulation. In one embodiment, the route of administration is oral.

The pharmaceutical compositions of the present disclosure may be manufactured by any of the methods well-known in the art, such as by conventional mixing, dissolving, granulating, dragee-making, levigating, emulsifying, encapsulating, entrapping, or lyophilizing processes. As noted above, the compositions can include one or more pharmaceutically acceptable excipients that facilitate processing of active molecules into preparations for pharmaceutical use.

Proper formulation is dependent upon the route of administration chosen. For injection, for example, the composition may be formulated in aqueous solutions, preferably in physiologically compatible buffers such as Hanks' solution, Ringer's solution, or physiological saline buffer. For transmucosal or nasal administration, penetrants appropriate to the barrier to be permeated are used in the formulation. Such penetrants are generally known in the art. In a preferred embodiment of the present disclosure, the present crystalline forms are prepared in a formulation intended for oral administration. For oral administration, it can be formulated readily by combining the crystalline forms with pharmaceutically acceptable excipients well known in the art. Such excipients enable the crystalline forms of the disclosure to be formulated as tablets, pills, dragees, capsules, liquids, gels, syrups, slurries, suspensions and the like, for oral ingestion by a subject. The crystalline forms may also be formulated in rectal compositions such as suppositories or retention enemas, e.g., containing conventional suppository bases such as cocoa butter or other glycerides.

Pharmaceutical preparations for oral use can be obtained using solid excipients, optionally grinding a resulting mixture, and processing the mixture of granules, after adding suitable auxiliaries, if desired, to obtain tablets or dragee cores. Suitable excipients are, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, microcrystalline cellulose and/or polyvinylpyrrolidone (PVP or povidone). If desired, disintegrating agents may be added, such as the cross-linked polyvinyl pyrrolidone, agar, croscarmellose sodium or alginic acid or a salt thereof such as sodium alginate. Also, wetting agents such as sodium dodecyl sulfate or magnesium stearate may be included.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the crystalline forms may be dissolved or suspended in suitable liquids, such as fatty oils, liquid paraffin, or liquid polyethylene glycols. In addition, stabilizers may be added. All formulations for oral administration should be in dosages suitable for such administration.

In one embodiment, the crystalline forms described herein can be administered transdermally, such as through a skin patch, or topically. In one aspect, the transdermal or topical formulations can additionally comprise one or multiple penetration enhancers or other effectors, including agents that enhance migration of the delivered compound. Transdermal or topical administration could be preferred, for example, in situations in which location specific delivery is desired.

For administration by inhalation, the crystalline forms for use according to the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, for example, gelatin, for use in an inhaler or insufflator may be formulated. These typically contain a powder mix of the crystalline form and a suitable powder base such as lactose or starch.

Compositions formulated for parenteral administration by injection, e.g., by bolus injection or continuous infusion can be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Formulations for parenteral administration include aqueous solutions or other compositions in water-soluble form.

Suspensions of the crystalline forms may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the crystalline forms to allow for the preparation of highly concentrated solutions. Alternatively, the active ingredient may be in powder form for constitution with a suitable vehicle, e.g., sterile pyrogen-free water, before use.

As mentioned above, the compositions of the present disclosure may also be formulated as a depot preparation. Such long acting formulations may be administered by implantation (for example, subcutaneously or intramuscularly) or by intramuscular injection. Thus, for example, the present crystalline forms may be formulated with suitable polymeric or hydrophobic materials (for example as an emulsion in an acceptable oil) or ion exchange resins, or as sparingly soluble derivatives, for example, as a sparingly soluble salt.

For any composition used in the various treatments embodied herein, a therapeutically effective dose can be estimated initially using a variety of techniques well known in the art. For example, in a cell culture assay, a dose can be formulated in animal models to achieve a circulating concentration range that includes the $IC_{50}$ as determined in cell culture. Dosage ranges appropriate for human subjects can be determined, for example, using data obtained from cell culture assays and non-human animal studies.

A therapeutically effective dose of a compound refers to that amount of the compound that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Compounds that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

Dosage amount and interval may be adjusted individually to provide plasma levels of the active moiety that are sufficient to modulate a desired parameter, e.g., endogenous erythropoietin plasma levels, i.e. minimal effective concentration (MEC). The MEC will vary for each compound but can be estimated from, for example, in vitro data. Dosages necessary to achieve the MEC will depend on individual characteristics and route of administration. Compounds or compositions thereof should be administered using a regimen which maintains plasma levels above the MEC for about 10-90% of the duration of treatment, preferably about 30-90% of the duration of treatment, and most preferably between 50-90%. In cases of local administration or selective uptake, the effective local concentration of the drug may not be related to plasma concentration. Alternatively, modulation of a desired parameter, e.g., stimulation of endogenous erythropoietin, may be achieved by 1) administering a loading dose followed by a maintenance dose, 2) administering an induction dose to rapidly achieve the desired parameter, e.g., erythropoietin levels, within a target range, followed by a lower maintenance dose to maintain, e.g., hematocrit, within a desired target range, or 3) repeated intermittent dosing.

The amount of compound or composition administered will, of course, be dependent on a variety of factors, including the sex, age, and weight of the subject being treated, the severity of the affliction, the manner of administration, and the judgment of the prescribing physician.

An effective dose (or therapeutically effective dose) can be estimated initially using a variety of techniques well known in the art. For example, in a cell culture assay, a dose can be formulated in animal models to achieve a circulating concentration range that includes the $IC_{50}$ as determined in cell culture. Dosage ranges appropriate for human subjects can be determined, for example, using data obtained from cell culture assays and non-human animal studies. In one embodiment, the dosage may be from 0.001 mg/kg to about 100 mg/kg. Typically, the dosage may be from about 0.002 mg/kg to about 50 mg/kg; from about 0.005 mg/kg to about 10 mg/kg; from about 0.008 mg/kg to about 1 mg/kg; from about 0.01 mg/kg to about 0.5 mg/kg; from about 0.05 mg/kg to about 0.4 mg/kg; or from about 0.15 mg/kg to about 0.4 mg/kg. For example, the dosage may be about 0.01 mg/kg; about 0.02 mg/kg; about 0.03 mg/kg; about 0.04 mg/kg; about 0.05 mg/kg; about 0.06 mg/kg; about 0.07 mg/kg; about 0.08 mg/kg; about 0.09 mg/kg; about 0.1 mg/kg; about 0.15 mg/kg; about 0.2 mg/kg; about 0.25 mg/kg; about 0.3 mg/kg; about 0.4 mg/kg; about 0.5 mg/kg; about 0.6 mg/kg; about 0.7 mg/kg; about 0.8 mg/kg; about 0.9 mg/kg; or about 1 mg/kg. The dosages may be administered at various intervals, for example, four times a day, three times a day, twice a day, every day, every other day, 1, 2, or 3 times a week, etc.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a crystalline form of the disclosure formulated in a compatible pharmaceutical excipient may also be prepared, placed in an appropriate container, and labeled for treatment of an indicated condition. Suitable conditions indicated on the label may include treatment of conditions, disorders, or diseases in which anemia is a major indication.

7. Method of Use

One aspect of the disclosure provides for use of one or more of a crystalline form of {[1-cyano-5-(4-chlorophenoxy)-4-hydroxy-isoquinoline-3-carbonyl]-amino}-acetic acid (Compound A), or a composition comprising one or more crystalline forms of Compound A, for the manufacture of a medicament for use in treating various conditions or disorders as described herein. It also provides methods of using the crystalline form, or composition or medicament thereof, to treat, pretreat, or delay progression or onset of various conditions or disorders as described herein. In one embodiment, the crystalline form of Compound A used in the method is Form 1. In one embodiment, the crystalline form of Compound A used in the method is Form 2.

The medicaments or compositions can be used to modulate the stability and/or activity of HIF, and thereby activate HIF-regulated gene expression. The crystalline form, or composition or medicament thereof, can be used in methods to treat, pretreat, or delay progression or onset of conditions associated with HIF including, but not limited to, anemic, ischemic, and hypoxic conditions. In various embodiments, the crystalline form, or composition or medicament thereof, is administered immediately following a condition producing acute ischemia, e.g., myocardial infarction, pulmonary embolism, intestinal infarction, ischemic stroke, and renal ischemic-reperfusion injury. In another embodiment, the crystalline form, or composition or medicament thereof, is administered to a patient diagnosed with a condition associated with the development of chronic ischemia, e.g., cardiac cirrhosis, macular degeneration, pulmonary embolism, acute respiratory failure, neonatal respiratory distress syndrome, and congestive heart failure. In yet another embodiment, the crystalline form, or composition or medicament thereof, is administered immediately after a trauma or injury. In other embodiments, the crystalline form, or composition or medicament thereof, can be administered to a subject based on predisposing conditions, e.g., hypertension, diabetes, occlusive arterial disease, chronic venous insufficiency, Raynaud's disease, chronic skin ulcers, cirrhosis, congestive heart failure, and systemic sclerosis. In still other embodiments, the crystalline form, or composition or medicament thereof, may be administered to pretreat a subject to decrease or prevent the development of tissue damage associated with ischemia or hypoxia.

The crystalline form, or compositions or medicaments thereof, can also be used to increase endogenous erythropoietin (EPO). The crystalline form, or composition or medicament thereof, can be administered to prevent, pretreat, or treat EPO-associated conditions, including, e.g., conditions associated with anemia and neurological disorders. Conditions associated with anemia include disorders such as acute or chronic kidney disease, diabetes, cancer, ulcers, infection with virus, e.g., HIV, bacteria, or parasites; inflammation, etc. Anemic conditions can further include those associated with procedures or treatments including, e.g., radiation therapy, chemotherapy, dialysis, and surgery. Disorders associated with anemia additionally include abnormal hemoglobin and/or erythrocytes, such as found in disorders such as microcytic anemia, hypochromic anemia, aplastic anemia, etc.

The disclosure is also directed to use of a crystalline form, or composition or medicament thereof, to treat, pretreat, or delay onset of a condition associated with a disorder selected from the group consisting of anemic disorders; neurological disorders and/or injuries including cases of stroke, trauma, epilepsy, and neurodegenerative disease; cardiac ischemia including, but not limited to, myocardial infarction and congestive heart failure; liver ischemia including, but not limited to, cardiac cirrhosis; renal ischemia including, but not limited to, acute kidney failure and chronic kidney failure; peripheral vascular disorders, ulcers, burns, and chronic wounds; pulmonary embolism; and ischemic-reperfusion injury.

The disclosure is also directed to a method of inhibiting the activity of at least one hydroxylase enzyme which modifies the alpha subunit of hypoxia inducible factor. The HIF hydroxylase enzyme may be a prolyl hydroxylase including, but not limited to, the group consisting of EGLN1, EGLN2, and EGLN3, described by Taylor (2001, Gene 275:125-132), and characterized by Aravind and Koonin (2001, Genome Biol 2:RESEARCH0007), Epstein et al. (2001, Cell 107:43-54), and Bruick and McKnight (2001, Science 294:1337-1340). The method comprises contacting the enzyme with an inhibiting effective amount of one or more crystalline form of Compound A.

While this disclosure has been described in conjunction with specific embodiments and examples, it will be apparent to a person of ordinary skill in the art, having regard to that skill and this disclosure, that equivalents of the specifically disclosed materials and methods will also be applicable to this disclosure; and such equivalents are intended to be included within the following claims.

EXAMPLES

Unless otherwise stated, the following abbreviations used throughout the specification have the following definitions:
d doublet
DCM dichloromethane, methylene chloride
DMF dimethylformamide
DMSO dimethylsulfoxide
DSC differential scanning calorimetry
EDTA ethylenediaminetetraacetic acid
eq. equivalent
EtOAc ethyl acetate
EtOH ethanol, ethyl alcohol
g gram
HPLC high performance liquid chromatography
hr or h hour
Hz Hertz
IPA iso-propyl alcohol, propan-2-ol
IPAc iso-propyl acetate
IR infrared
J coupling constant
kg kilogram
kV killivolts
L liter
LOD limit of detection
M molar
m multiplet
mA milliampere
Me methyl
MeO methoxy
MeOH methanol
mg milligram
min. minute
mL milliliter
mm millimeter
MTBE methyl tert-butyl ether
N normal
NaOMe sodium methoxide
nM nanomolar
NMP n-methyl pyrrolidone
NMR nuclear magnetic resonance
s singlet
RH relative humidity
SS-NMR Solid state nuclear magnetic resonance
TGA thermal gravimetric analysis
THF tetrahydrofuran
XRPD X-ray powder diffraction
VT-XRPD variable temperature X-ray powder diffraction
DSC—Differential Scanning Calorimetry DSC data were collected on a Mettler DSC 823e equipped with a 50 position auto-sampler. The instrument was calibrated for energy and temperature using certified indium. Typically 0.5-3 mg of each sample, in a pin-holed aluminium pan, was heated at 10° C./min from 25° C. to 350° C. A nitrogen purge at 50 ml/min was maintained over the sample. The instrument control and data analysis software was STARe v 9.10.

Modulated DSC data were collected on a TA Instruments Q2000 equipped with a 50 position auto-sampler. The calibration for thermal capacity was carried out using sapphire and the calibration for energy and temperature was carried out using certified indium. Typically 0.5-2 mg of each sample, in a pin-holed aluminium pan, was heated at using an underlying heating rate of 2° C./min and temperature modulation parameters of ±0.2° C./min and 40 seconds. The instrument control software was Advantage for Q Series v2.8.0.392 and Thermal Advantage v4.8.3 and the data were analysed using Universal Analysis v4.3A.

NMR—Nuclear Magnetic Resonance: $^1$H and $^{13}$C NMR

NMR spectra were collected on a Bruker 400 MHz instrument equipped with an auto-sampler and controlled by a DRX400 console. Automated experiments were acquired using ICON-NMR v4.0.4 (build 1) running with Topspin v 1.3 (patch level 8) using the standard Bruker loaded experiments. For non-routine spectroscopy, data were acquired through the use of Topspin alone. Samples were prepared in $d_6$-DMSO, unless otherwise stated. Off-line analysis was carried out using ACD SpecManager v 9.09 (build 7703).

TGA—Thermo Gravimetric Analysis

TGA data were collected on a Mettler TGA/SDTA 851e equipped with a 34 position auto-sampler. The instrument was temperature calibrated using certified indium. Typically 5-30 mg of each sample was loaded onto a pre-weighed aluminium crucible and was heated at 10° C./min from ambient temperature to 350° C. A nitrogen purge at 50 ml/min was maintained over the sample. The instrument control and data analysis software was STARe v 9.10.

XRPD—X-Ray Powder Diffraction

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Gael multilayer mirror coupled with a pinhole collimator of 0.3 mm.

The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample would be exposed to the X-ray beam for 120 seconds. The software used for data collection was GADDS for WNT 4.1.16 and the data were analysed and presented using Diffrac Plus EVA v 9.0.0.2 or v 13.0.0.2.

Samples run under ambient conditions were prepared as flat plate specimens using powder as received without grinding. Approximately 1-2 mg of the sample was lightly pressed on a glass slide to obtain a flat surface.

Samples run under non-ambient conditions were mounted on a silicon wafer with heat-conducting compound. The sample was then heated to the appropriate temperature at approximately 20° C.·min$^{-1}$ and subsequently held isothermally for approximately 1 minute before data collection was initiated.

X-Ray Powder Diffraction patterns were also collected on a Bruker D8 diffractometer using Cu Kα radiation (40 kV, 40 mA), θ-2θ goniometer, and divergence of V4 and receiving slits, a Ge monochromator and a Lynxeye detector. The instrument was performance checked using a certified Corundum standard (NIST 1976). The software used for data collection was Diffrac Plus XRD Commander v 2.5.0 and the data were analysed and presented using Diffrac Plus EVA v 11.0.0.2 or v 13.0.0.2.

Samples were run under ambient conditions as flat plate specimens using powder as prepared in Examples 1 and 2. Approximately 50-100 mg of the sample was gently packed into a cavity cut into polished, zero-background (510) silicon wafer. The sample was rotated in its own plane during analysis. The details of the data collection are:

Angular range: 2 to 42°2θ
Step size: 0.05°2θ
Collection time: 0.5 s·step$^{-1}$.

Example 1

Preparation of Crystalline Form 1 of Compound A

Method 1

Ethyl 1-cyano-5-(4-chlorophenoxy)-4-hydroxy-isoquinoline-3-carboxylate (74.4 g, see U.S. Pat. No. 7,928,120 for general synthetic methods) and glycine (302.9 g, 20 eq.) were suspended in methanol (4.0 L) at room temperature. NaOMe (25%, 692 mL, 15 eq.) was added, and the mixture was heated to reflux and stirred for overnight. After LC-MS showed completion of reaction, the suspension was cooled and acidified to pH-3 with 1 N HCl. The resulting mixture was filtered, washed with water and dried in a vacuum oven (40° C.) to constant weight to give an off-white solid, Compound A, Form 1 (77.8 g).

Method 2

Compound A (12 g, see U.S. Pat. No. 7,928,120 for general synthetic methods) was suspended in acetonitrile (620 mL). This mixture was stirred and heated to reflux for 30 minutes giving a clear pale yellow solution. It was slowly cooled to room temperature and then to 5° C., stirred for 30 minutes, filtered, washed with cold acetonitrile, and dried in a vacuum oven (65° C.) to constant weight to give a white solid, Compound A, Form 1 (10.0 g).

Method 3

Compound A (0.5 g) was suspended in neat acetic acid (10 mL) and stirred at 80° C. for 16 h. This mixture was cooled to room temperature, filtered, and dried in a vacuum oven (80° C.) to constant weight to give an off white solid, Compound A, Form 1 (0.44 g).

XRPD of Compound A, form 1 showed the pattern in FIG. 1. The peaks were at 7.7, 11.2, 13.8, 14.7, 15.3, 15.8, 18.3, 21.1, 22.2, 23.2, 25.2, 25.9° and 27.7°2θ±0.2°2θ, as determined on a diffractogram using Cu—Kα radiation. For characterization, at least one, preferably at least two, more preferably at least three of these peaks were used.

DSC analysis of Compound A, form 1 showed the pattern in FIG. 2. The DSC curve in FIG. 2 showed an endotherm at about 251° C. and an exotherm at about 210° C.

$^1$H-NMR of Compound A in solution was consistent with its structure. $^1$H-NMR (400 MHz, dmso-d$_6$, 298K): 14.92 (s, 1H), 12.88 (bs, 1H), 9.61 (bt, 1H, J 6.06), 8.10 (dd, 1H, J 1.01, 8.34), 8.03 (dd, 1H, J 7.58, 8.34), 7.51 (dd, 1H, J 1.01, 7.58), 7.42 (d, 2H, J 9.09), 6.99 (d, 2H, J 9.09) and 4.02 (d, 2H, J 6.32) ppm.

Example 2

Preparation of Crystalline Form 2 of Compound A

Method 1

Sodium salt of Compound A (1.22 Kg) was dissolved in water, stirred and heated to 80° C. Acetic acid (830 g) was added slowly over 3 h. This mixture was stirred for 2 h at 80° C. (to ensure that solid converts to Form 2). This was cooled to 20-25° C., stirred for 1 h, filtered, and washed with water (31 L). Solid was dried in a vacuum oven (80° C.) to constant weight to give off-white solid, Compound A, Form 2 (880 g).

Method 2

Compound A (7.5 g) and 1 N NaOH (23.6 mL) was stirred in water and heated to 80° C. until solids were dissolved. Acetic acid (2.25 g) was added slowly. The mixture was stirred at 80° C. for 2 h. This mixture was cooled to about 20° C., filtered, washed with water, and dried in a vacuum oven (80° C.) to constant weight to give a white solid, Compound A, Form 2 (7.25 g).

Method 3

Compound A (0.6 g) was refluxed with isopropyl acetate (about 30 mL) overnight, cooled to room temperature, filtered, and washed with isopropyl acetate, and dried to constant weight to give a white solid, Compound A, Form 2 (0.4 g).

Method 4

Compound A (26 g) was suspended in water, heated to 80° C., stirred for 1 h, cooled to room temperature, filtered, washed with water, and dried in a vacuum oven (80° C.) to constant weight to give an off white solid, Compound A, Form 2 (25.3 g).

XRPD of Compound A, form 2 showed the pattern in FIG. 3. The peaks were at 7.2, 8.1, 10.6, 11.5, 13.9, 14.5, 16.2, 19.3, 21.5, 21.9, 22.7, 23.2, 24.5, 25.9, 26.6, 27.8, and 29.1°2θ±0.2°2θ, as determined on a diffractogram using Cu—Kα radiation. For characterization, at least one, preferably at least two, more preferably at least three of these peaks were used.

DSC analysis of Compound A, form 2 showed the pattern in FIG. 4. The DSC curve in FIG. 4 showed an endotherm at about 249° C.

$^1$H-NMR of Compound A in solution was consistent with its structure. $^1$H-NMR (400 MHz, dmso-d$_6$, 298K): 14.92 (s, 1H), 12.88 (bs, 1H), 9.61 (bt, 1H, J 6.06), 8.10 (dd, 1H, J 1.01, 8.34), 8.03 (dd, 1H, J 7.58, 8.34), 7.51 (dd, 1H, J 1.01, 7.58), 7.42 (d, 2H, J 9.09), 6.99 (d, 2H, J 9.09) and 4.02 (d, 2H, J 6.32) ppm.

Example 3

Stability of Form 1 and Form 2 of Compound A

Cross-seeding Experiments

A solid mixture containing about 50% of Form 1 and about 50% of Form 2 (obtained from maturation in IPAc) (~10 mg) was placed in six different vials. Three of these vials were treated with DCM (~50 μL in each one) and the other three were treated with IPAc (~50 μL in each one). Slurries of the solid mixture in DCM and IPAc were shaken at 5° C., 25° C. and 50° C. for 10 days.

The solids from DCM, after drying at ambient conditions, were analysed by XRPD, the crystalline patterns matched Form 1.

The solids from IPAc, after drying at ambient conditions, were analysed by XRPD, the crystalline patterns matched Form 2.

Maturation of Form 1 in Water with Seeds of Form 2

A suspension of a solid mixture of Form 1 and Form 2 (1:1) in water was incubated at 50° C./room temperature (4 h-cycles), and at 75% RH for four days. After this time, the solid was analysed by XRPD. The crystalline pattern matched Form 2, and no traces of Form 1 were detected in this analysis.

Maturation of Form 1 in Water without Seeds of Form 2

Form 1 was suspended in water and incubated at 50° C./room temperature (4 h-cycles), and at 75% RH. In this case, the transformation of Form 1 into Form 2 was slower. After 4 days, there was clear indication of Form 2 forming, but there was also a significant amount of Form 1 remaining After 15 days under these conditions, Form 1 had completely turned to Form 2.

Stability of Form 2

Form 2 remained unchanged after a week in a humidity chamber at 40° C. and 75% RH.

Reflux Form 1 in Water

Form 1 was refluxed in water and the crystallinity of the solid was monitored by XRPD. After 2.5 h, several new diffraction peaks corresponding to Form 2 could already be observed. After 10 h at reflux, the transformation of Form 1 into Form 2 was complete.

Stability of Form 1 in Water at 25° C.

Form 1 was suspended in water at 25° C., and the crystallinity of the solid was analysed by XRPD over a period of time. No changes were observed in the crystalline pattern of Form 1 after six days in an aqueous suspension at 25° C.

These studies indicate that Form 2 is thermodynamically more stable than Form 1.

Example 4

Preparation and Characterization of Solvates of Compound a

Preparation and Characterization by XRPD

Figure 5:
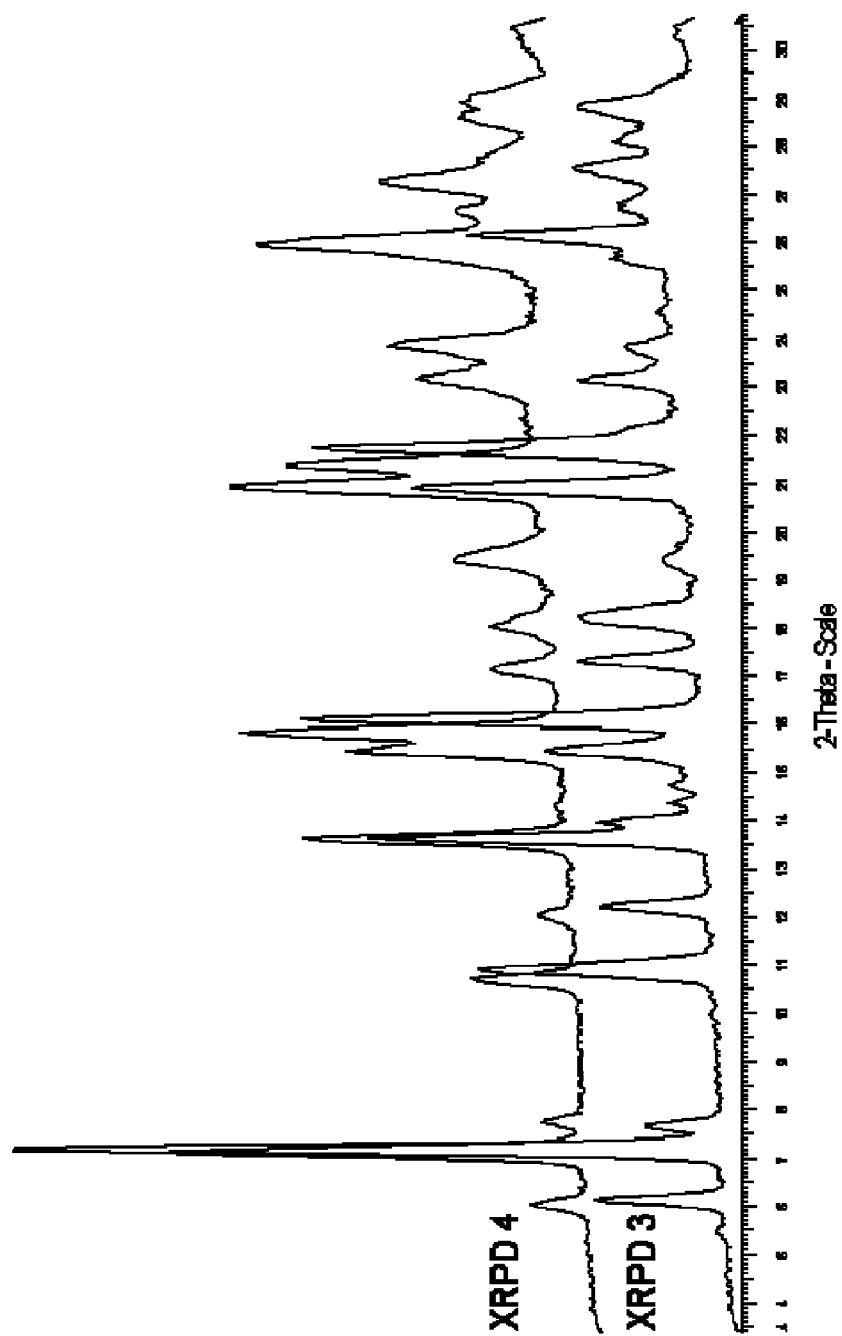
FIG. 5 shows XRPD patterns for solvates of Compound A, XRPD3 and XRPD4.
Figure 6:
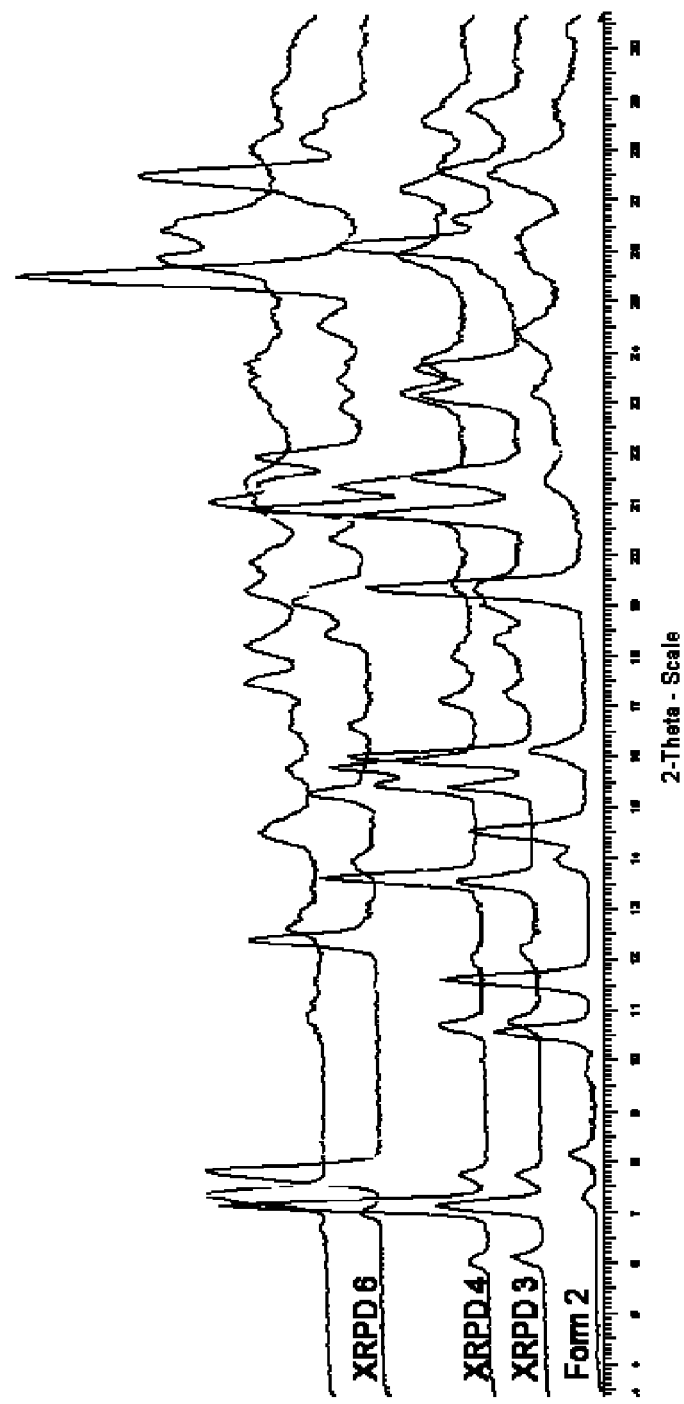
FIG. 6 shows XRPD patterns for Compound A, Form 2, and solvates of Compound A, XRPD 3, XRPD 4, XRPD 5, XRPD 6 and XRPD 7.

Form 1 (200 mg) was suspended in the corresponding solvent (see Table 1) and incubated at 40° C./room temperature (4 h cycles) for 16 h. The solvent was then removed under vacuum (except the experiment in 1,4-dioxane, which was dried under ambient conditions) and the solids were analysed by XRPD. FIG. 5 showed XRPD patterns for solvates of Compound A, XRPD3 and XRPD4. FIG. 6 showed XRPD patterns for Compound A, Form 2, and solvates of Compound A, XRPD3, XRPD4, XRPD5, XRPD6 and XRPD7.

TABLE 1

Solvates of Compound A

| Solvent | Solvate characterized by XRPD | Stability at 40° C./ 75% RH |
| --- | --- | --- |
| IPAc (10 volume) | Form 2 | Form 2 |
| THF (3 volume) | XRPD 3 | Form 1 |
| Toluene (5 volume) | XRPD 4 | Form 1 |
| DMF (4 volume) | XRPD 5 | Form 2 |
| NMP (4 volume) | XRPD 6 | Form 2 - incomplete |
| 1,4-dioxane (5 volume) | XRPD 7 | Form 2 |

Stability

The solids were then stored in the humidity chamber at 40° C. and 75% RH for a week to assess their stability under these conditions, and re-analysed by XRPD.

Form 2 remained unchanged after a week in a humidity chamber at 40° C. and 75% RH. Both XRPD 3 and XRPD 4 solids transformed into Form 1 after storage for a week under these conditions. XRPD 5, XRPD 6 and XRPD 7 solids changed into Form 2 after one week at 40° C. and 75% RH. In the case of the solid obtained from NMP (XRPD 6), the transformation was not complete, and some peaks from the initial crystalline forms could still be observed in its powder pattern. The results are summarized in Table 1.

Figure 7:
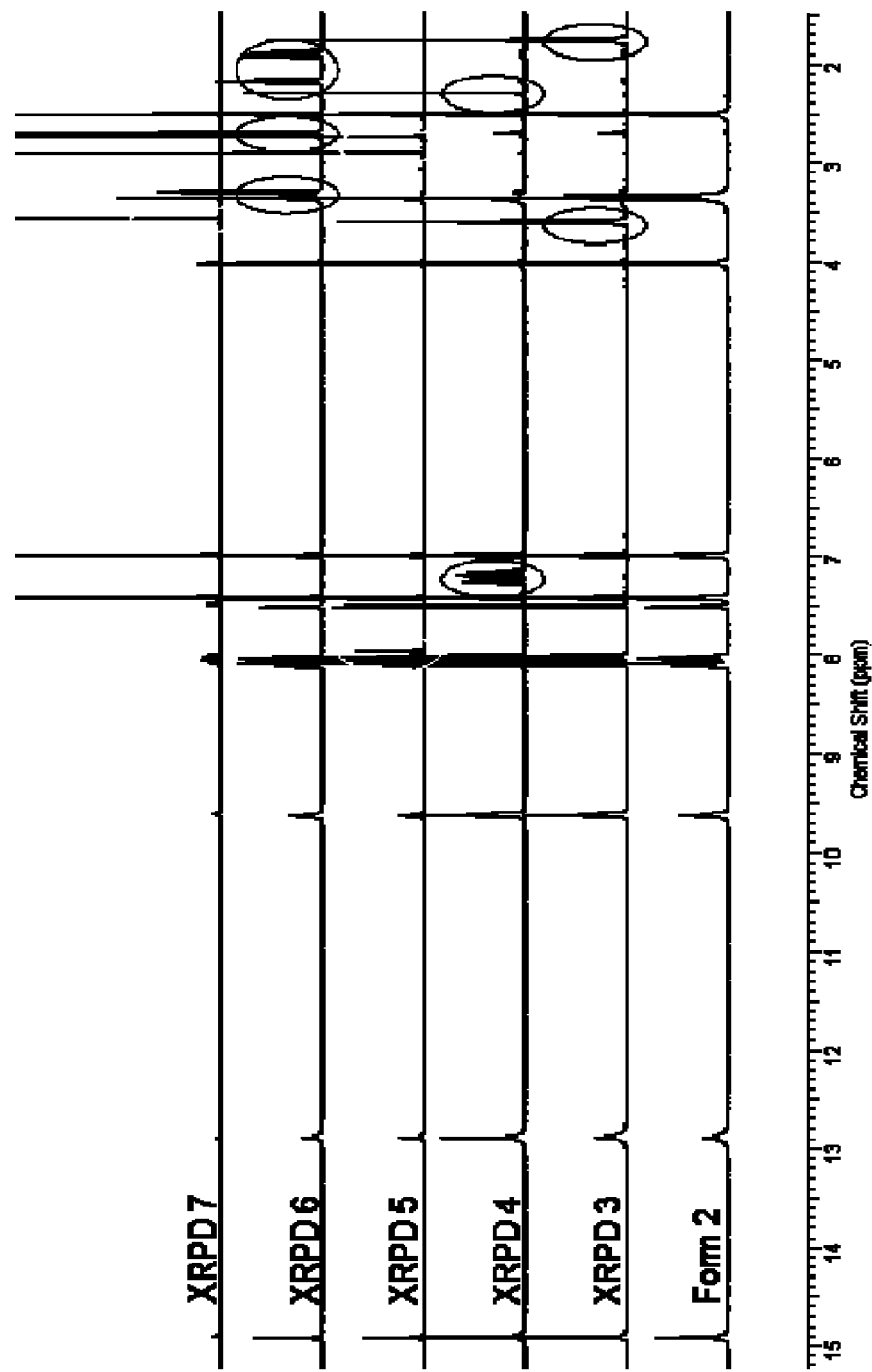
FIG. 7 shows $^1$H-NMR spectra for Compound A, Form 2, and solvates of Compound A, XRPD 3, XRPD 4, XRPD 5, XRPD 6 and XRPD 7.

$^1$H-NMR Analysis $^1$H-NMR analyses were carried out for Compound A, Form 2, and solvates of Compound A (FIG. 7). The spectra were consistent with the proposed structure. Some residual solvent was identified and quantified for the solids with crystalline patterns XRPD 3, XRPD 4, XRPD 5, XRPD 6 and XRPD 7, by integration of the signals highlighted in FIG. 7. This result suggested that these solids were solvates rather than new polymorphs.

Thermal Analysis

Thermal analyses were also carried out for Compound A, Form 2, and solvates of Compound A.

No weight loss was observed in the TGA thermogram for Form 2 until degradation started at ~260° C. The DSC thermogram only showed an endothermic event, which corresponded with the melt of Form 2 (onset 249° C., melting enthalpy −132.5 J/g).

A weight loss of ~7.5% was observed in the TGA thermogram for the XRPD 3 solid between 45 and 140° C. This weight loss correlated with the amount of residual THF observed in the $^1$H-NMR spectrum and it was associated with a broad endothermic event in the DSC thermogram, probably desolvation to Form 1. A small exothermic event with an onset ~200° C. indicated that a solid-solid transition of Form 1 to produce Form 2 had taken place. The material then melted at 251° C. Degradation of the sample started at ~260° C.

A weight loss of ~4.5% was observed in the TGA thermogram for the XRPD 4 solid between 60 and 160° C. This weight loss correlated with the amount of residual toluene observed in the $^1$H-NMR spectrum and it was associated with an endothermic event in the DSC thermogram, probably desolvation to Form 1. A small exothermic event with an onset ~193° C. indicated that a solid-solid transition of Form 1 to produce Form 2 had taken place. The material then melted at 251° C. Degradation of the sample started at ~260° C.

A weight loss of ~15.3% was observed in the TGA thermogram for the XRPD 5 solid between 100 and 150° C. This weight loss correlated with the amount of residual DMF observed in the $^1$H-NMR spectrum and it was associated with an endothermic event in the DSC thermogram, probably desolvation to produce Form 2. The absence of the exothermic event at ~200° C. observed for XRPD 3 and XRPD 4 indicated that desolvation of this material did not produce Form 1 but Form 2, which was confirmed by the melt at 250° C. Degradation of the sample started at ~260° C.

A weight loss of ~19.8% was observed in the TGA thermogram for the XRPD 6 solid between 100 and 170° C. This weight loss correlated with the amount of residual NMP observed in the $^1$H-NMR spectrum and it was associated with an endothermic event in the DSC thermogram, probably desolvation to produce Form 2. As for the XRPD 5 material, desolvation did not produce Form 1 but Form 2. The material then melted at 250° C. Degradation of the sample started at ~260° C.

A weight loss of ~16.9% was observed in the TGA thermogram for the XRPD 7 solid between 80 and 110° C. This weight loss correlated with the amount of residual 1,4-dioxane observed in the $^1$H-NMR spectrum and it was associated with an endothermic event in the DSC thermogram, probably desolvation to produce Form 2. The material then melted at 249° C. Degradation of the sample started at ~260° C.

Example 5

Compound A Increases Hemoglobin and Hematocrit Levels in Mice

Compound A (2, 6, 20, 60, 100 or 200 mg/kg as an oral gavage) or vehicle control were administered orally 3 times in 1 week on Monday, Wednesday, and Friday (4-8 male Swiss Webster mice/group). Three days after the last dose, all animals were euthanized and blood and serum were collected for complete blood counts (CBC) and serum chemistry.

Figure 8:
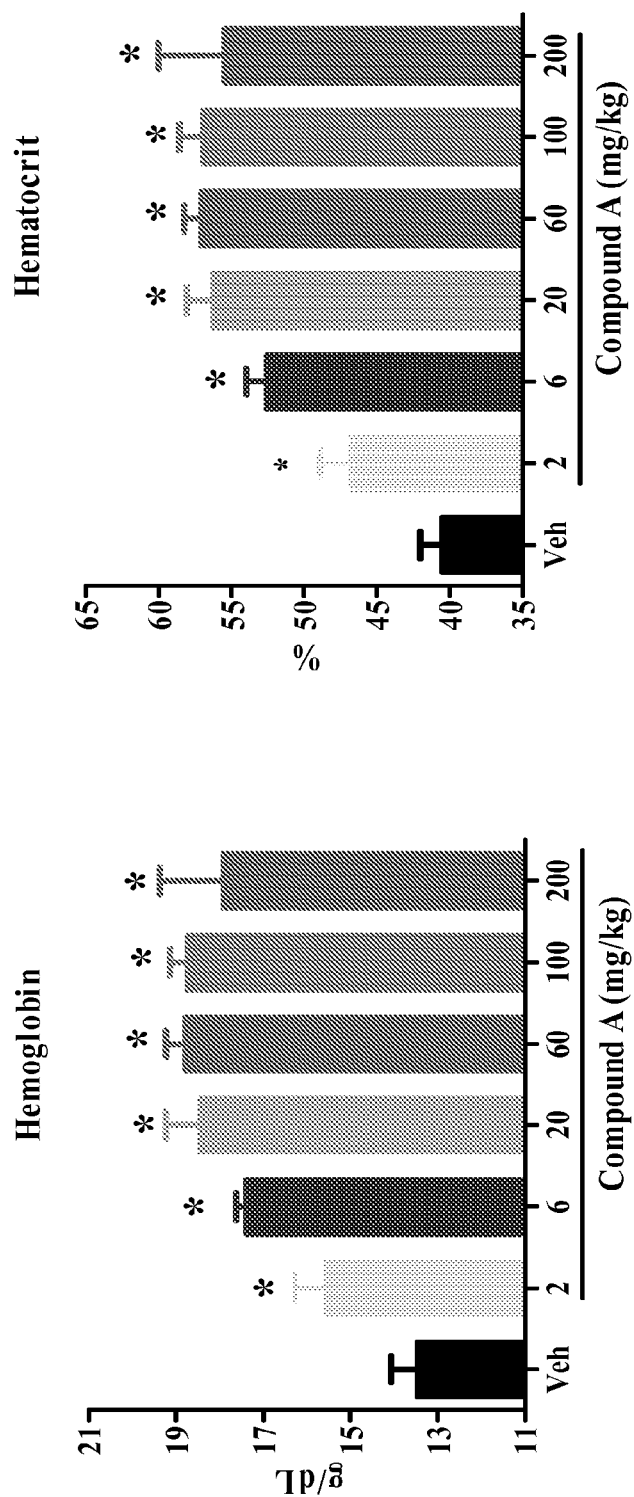
FIG. 8 demonstrates that Compound A increases hematocrit and hemoglobin following 1 week of intermittent dosing in mice.

Mean hemoglobin (Hb), hematocrit (HCT), and red blood counts (RBC) levels were significantly higher in all Compound A dose groups when compared to vehicle control (FIG. 8). Mean levels for all three parameters were dose-dependent at doses between 2 and 20 mg/kg, reaching a plateau between 20 and 60 mg/kg. Hb levels increased by more than 1 g/dL at the lowest dose tested, 2 mg/kg in this 1-week study in Swiss Webster mice. Compound A administration resulted in dose-dependent significant increases in hematology parameters of erythropoiesis.

Example 6

Compound A Increases Hemoglobin and Hematocrit Levels in Monkeys

Male cynomolgus monkeys (n=5/dose group) received daily oral administration of 0, 0.1, 0.3, 1, 3, 10 and 30 mg/kg Compound A for 14 consecutive days. Blood was collected for complete blood counts (CBC), once predose, and prior to dosing on Days 8 and 14.

Figure 9:
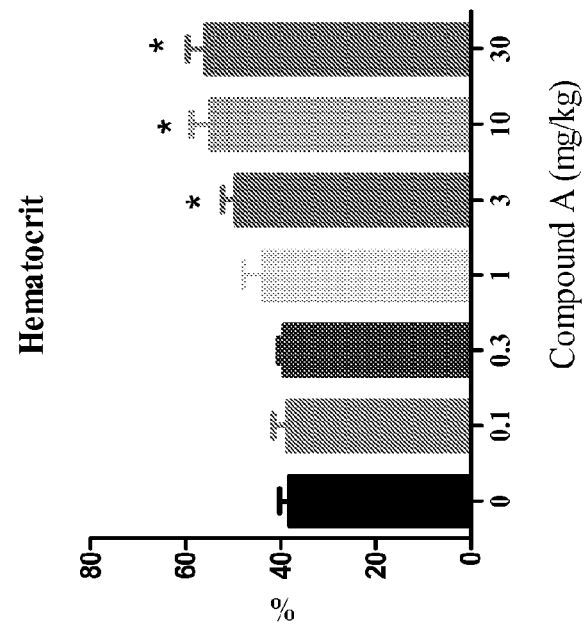
FIG. 9 demonstrates that Compound A increases hematocrit and hemoglobin following 2 weeks of daily dosing in normal monkeys.
Figure 9:
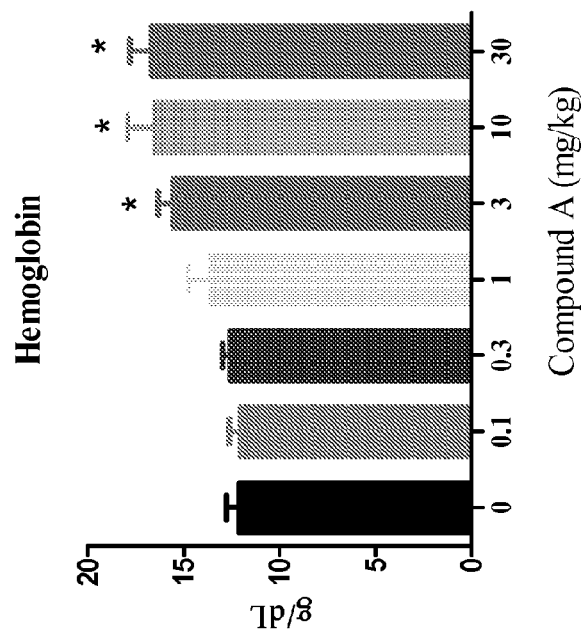

Oral administration (oral gavage) of Compound A at doses of 0, 0.1, 0.3, 1, 3, 10 and 30 mg/kg to cynomolgus monkeys for 14 consecutive days was associated with changes in hematology at ≥1 mg/kg/day. On Days 8 and 14, there were dose-related increases in reticulocytes (RETI) (54% to 724%) at ≥1 mg/kg and at ≥3 mg/kg/day, increases in RBC (13% to 41%), Hb (18% to 38%) and HCT (14% to 46%). FIG. 9 shows the HCT, Hb, and RBC levels following 2 weeks of daily dosing.

Example 7

Treatment of Anemia of Chronic Disease

Anemia of chronic disease (ACD) is associated with various inflammatory conditions, including arthritis and neoplastic disease. This anemia is characterized by inadequate EPO production, alterations in iron metabolism, reduced red blood cell lifespan, and impaired erythropoietic response of the bone marrow.

Female Lewis rats were challenged with peptidoglycan-polysaccharide polymers (PG-PS) to induce arthritis and anemia. Arthritis and anemia were allowed to develop for 28 days prior to initiation of treatment with Compound A (oral gavage, 8 or 20 mg/kg) or vehicle (n=8/group). Treatments were administered 3 times per week (Monday, Wednesday, and Friday), for 2 weeks. Progression of the model was monitored by measurement of paw swelling and hematology parameters. Blood samples were analyzed for hematopoiesis and iron parameters. The study also included three non-challenged control groups (n=5/group) that were injected with saline rather than PG-PS and then treated with vehicle or Compound A (8 or 20 mg/kg) as described for the PG-PS animals.

Challenge with PG-PS polymers in female Lewis rats resulted in anemia that was apparent 4 weeks after PG-PS challenge. This model exhibited features of functional iron deficiency including microcytosis (decreased mean cell volume) and hypochromia (decreased mean corpuscular hemoglobin), decreased serum iron and increased total iron binding capacity (TIBC) and unsaturated iron binding capacity (UIBC), and features of anemia including significantly reduced hemoglobin, hematocrit, and red blood cell count. In addition to anemia, PG-PS-challenged rats developed systemic inflammation and arthritis, as indicated by elevated white blood cell counts and swelling of the extremities. Anemic PG-PS-challenged animals treated with vehicle did not exhibit significant changes in hematologic parameters over the course of the study.

Figure 10:
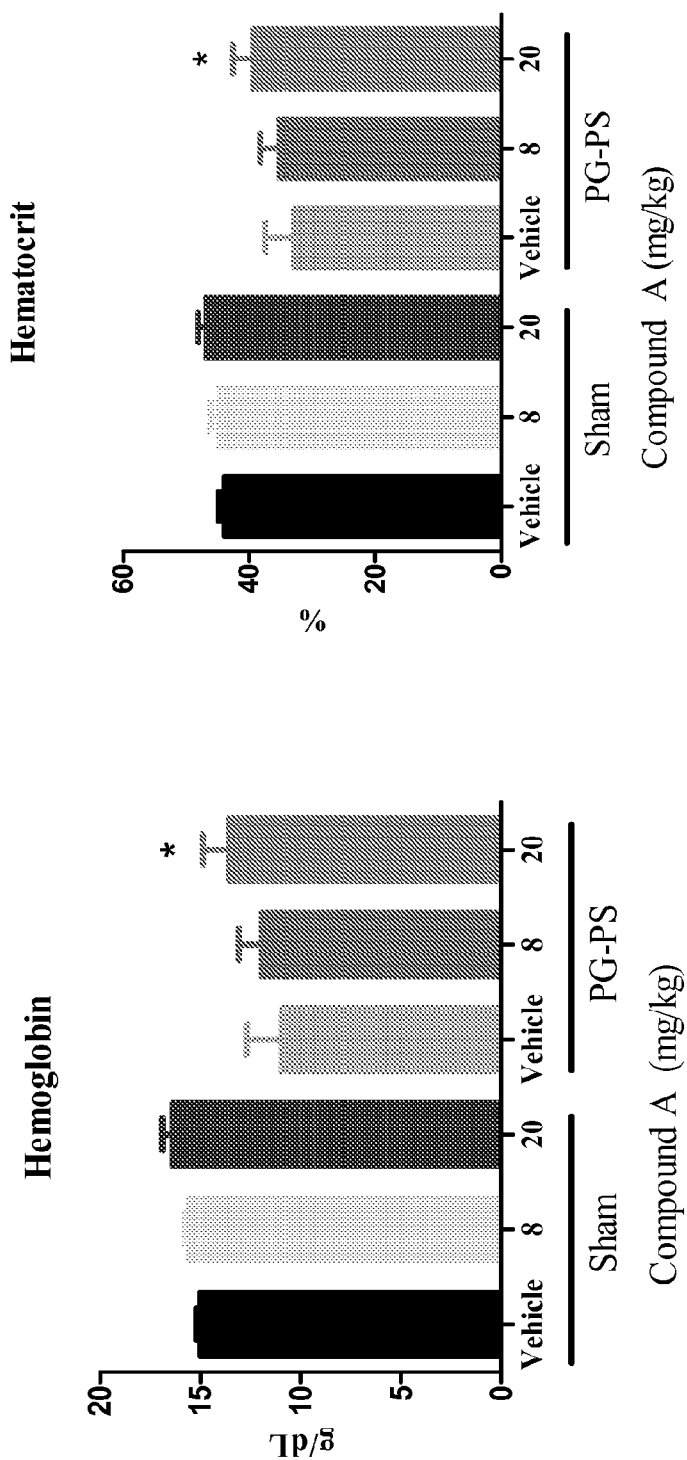
FIG. 10 demonstrates that Compound A increases hemoglobin and hematocrit in anemia of chronic disease in rats.

Intermittent treatment with Compound A (8 or 20 mg/kg) for 2 weeks corrected Hb, HCT, RBC, MCH decreases, and TIBC increases induced by PG-PS challenge, with statistically significant effects at 20 mg/kg dose (FIG. 10).

In summary, intermittent Compound A treatment significantly alleviated anemia associated with anemia of chronic disease.

Example 8

Treatment of Anemia Induced by Chronic Kidney Disease

The kidney is the major source of erythropoietin production in the adult mammal; therefore, anemia and decreased erythropoietin production is a common sequelae to renal failure. The rat remnant kidney model (induced by 5/6 nephrectomy) is a well-established model of anemia of progressive renal failure.

Female Wistar rats underwent subtotal nephrectomy (5/6) surgery to induce chronic kidney disease by ligating the left kidney to infarct 2/3 of the kidney while the right kidney underwent simultaneous total nephrectomy. As a control, additional animals underwent a sham surgery, without nephrectomy. Five weeks after surgery, anemia and chronic kidney disease in the nephrectomized animals were confirmed by clinical pathology and animals were then assigned to one of three treatment groups (n=8/group) and treated with 0 (vehicle), 8 or 20 mg/kg Compound A. The sham group (n=8) received 0 mg/kg (vehicle). Starting 6 weeks after surgery, all animals were dosed TIW (on Monday, Wednesday, and Friday) via oral gavage for 2 weeks. Whole blood samples were collected 5, 7, and 8 weeks after surgery.

Figure 11:
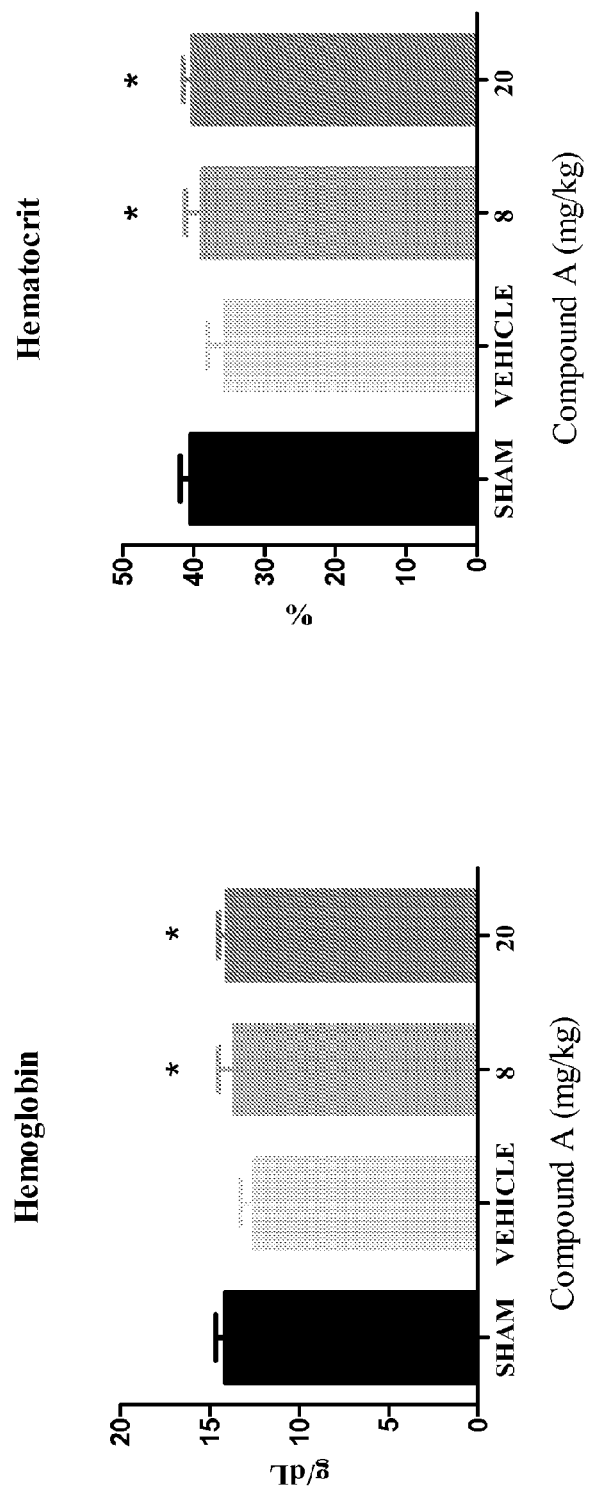
FIG. 11 demonstrates that Compound A alleviates anemia of chronic kidney disease in rats.

Nephrectomized animals exhibited classic features of anemia, namely, reduced Hb, HCT and RBC compared to the sham group, as well as increased systolic blood pressure at 5 and 8 weeks postsurgery. In addition, vehicle-treated nephrectomized animals exhibited chronic kidney disease by 5 weeks postsurgery, apparent in significant changes in serum chemistry parameters. After 2 weeks of treatment, Compound A administration at 8 and 20 mg/kg significantly elevated Hb, HCT, and RBC compared to vehicle controls (FIG. 11). Administration of 20 mg/kg Compound A normalized all three parameters to levels similar to the (non-anemic) sham control group. In addition, Compound A treatments appeared to cause higher MCV and MCH values in nephrectomized animals; however, only MCV at 20 mg/kg was significantly higher after 2 weeks of treatment.

It was concluded that intermittent treatment of Compound A for 2 weeks corrected anemia and improved iron utilization as evidenced by partial correction of the microcytosis and hypochromia associated with 5/6 nephrectomy.

Example 9

Compound a Increases Erythropoietin, Reticulocyte and Hemoglobin Levels in Human A single dose of Compound A (Form 2, capsules) was administered orally to healthy male volunteers. Compound A was provided in 1 mg and 5 mg capsules with the dose being rounded to the nearest whole capsule. In cohorts 1-4 the doses were 0.05 mg/kg, 0.15 mg/kg, 0.3 mg/kg and 0.4 mg/kg respectively. The time points for blood collection were: predose, 8, 12, 16, 20, 24, 30, 48, 72, 96 and 120 hours, days 8, 10, 12, and 15 post dose.

Erythropoietin

Figure 12:
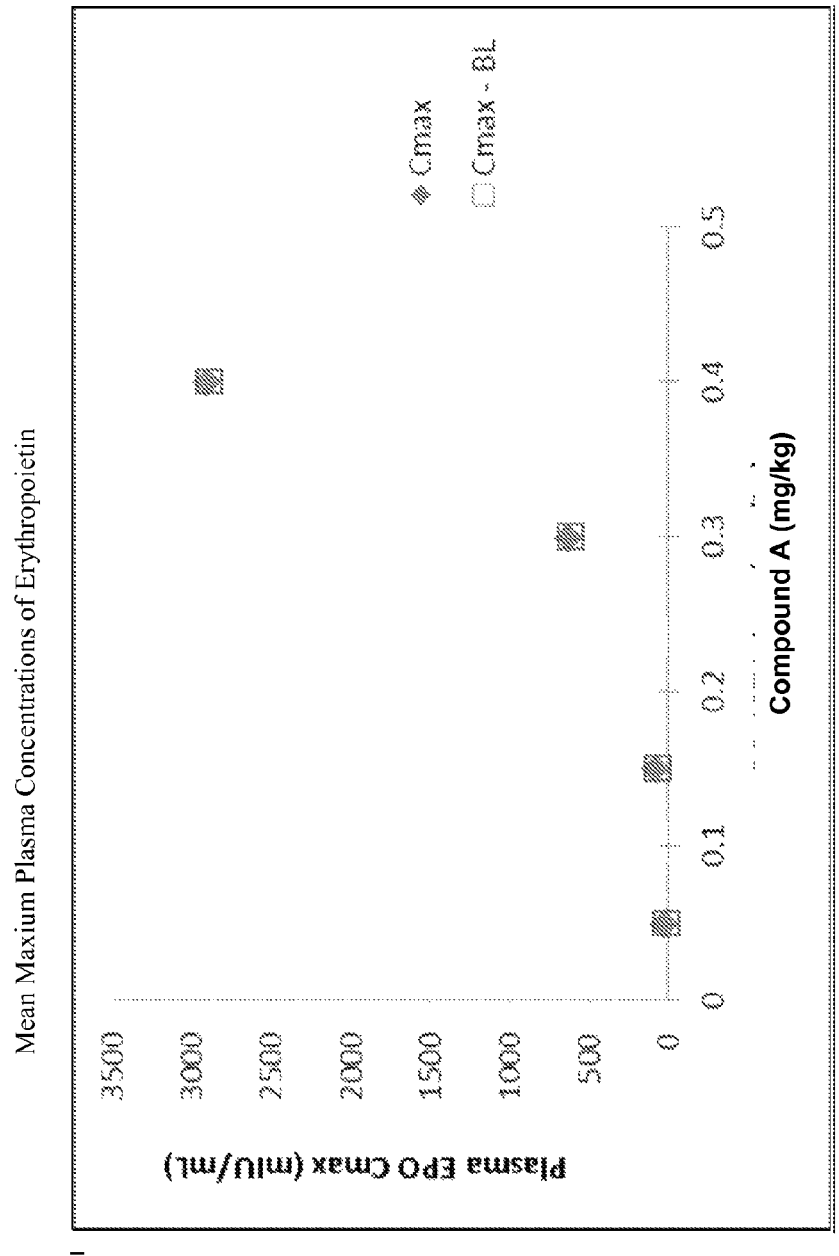
FIG. 12 shows that Compound A increases mean maximum plasma levels of erythropoietin in human.

FIG. 12 shows that mean maximum plasma levels of erythropoietin increase after dosing with Compound A.

In cohort 1, all subjects had increased plasma erythropoietin concentrations compared to baseline (pretreatment) after dosing with Compound A. Peak erythropoietin levels occurred at approximately 16.8 hours with a mean maximum plasma erythropoietin concentration of 27.2 mIU/mL compared with mean plasma erythropoietin concentration of 11.4 mIU/mL at baseline.

In cohort 2 all subjects had increased plasma erythropoietin concentrations after dosing with Compound A which increased approximately proportional to dose with the exception of one subject who showed a more robust erythropoietin response. Peak erythropoietin levels occurred at a mean of 14 hours after dosing with Compound A with a median maximum erythropoietin concentration of 81.7 mIU/ml. Mean erythropoietin levels trended back to baseline after approximately 5 days.

In cohort 3, peak erythropoietin levels occurred at a mean of 23 hours after dosing with an average maximum concentration of approximately 620 mIU/mL. Erythropoietin levels increased more than proportional to dose in cohort 3 compared to cohort 2.

In cohort 4, all subjects had increased plasma erythropoietin concentrations after dosing with Compound A compared to baseline (pretreatment). Maximum Erythropoietin (EPO) concentrations (Cmax) and baseline subtracted EPO Cmax (Cmax−BL) increased more than proportional to dose between cohort 3 (0.3 mg/kg) and cohort 4 (0.4 mg/kg) as shown in FIG. 12. The mean maximum plasma erythropoietin concentration for all subjects in Cohort 4 was 2,900 mIU/mL pending re-analysis of one sample that was above the upper limit of quantitation. The median time to maximum EPO concentration was 20 hours.

Reticulocyte Counts

There was a trend of increased reticulocyte counts in Cohorts 1-4 suggesting that Compound A was active at its biological target thereby eliciting an erythropoietic response (Table 2).

TABLE 2

Changes in Reticulocyte Counts

| | Reticulocyte values (% baseline ± SD) | | | |
|---|---|---|---|---|
| | Cohort 1 0.05 mg/kg (N = 5) | Cohort 2 0.15 mg/kg (N = 7) | Cohort 3 0.3 mg/kg (N = 6) | Cohort 4 0.4 mg/kg (N = 6) |
| Day 0 | 100 | 100 | 100 | 100 |
| Day 3 | 104 ± 8 | 111 ± 19 | 127 ± 3 | 163 ± 21 |
| Day 5 | 111 ± 10 | 121 ± 22 | 141 ± 22 | 134 ± 22 |
| Day 8 | 120 ± 20 | 180 ± 53 | 231 ± 40 | 376 ± 60 |

Hemoglobin Levels

In Cohort 1, mean hemoglobin levels did not change from Day 0 to Day 8. In cohort 2, hemoglobin mean increased by 0.3 g/dL on Day 8; in cohort 3, mean hemoglobin increased by 0.8 g/dL on Day 8; and in cohort 4 mean hemoglobin increased by 0.7 g/dL on Day 8 and by 1.1 g/dL on Day 15.

These data demonstrate that Compound A, when administered as crystalline Form 2, is effective to increase plasma EPO, increase reticulocyte levels, and increase mean hemoglobin levels.

What is claimed is:

1. Crystalline Form 1 of Compound A having the structure:

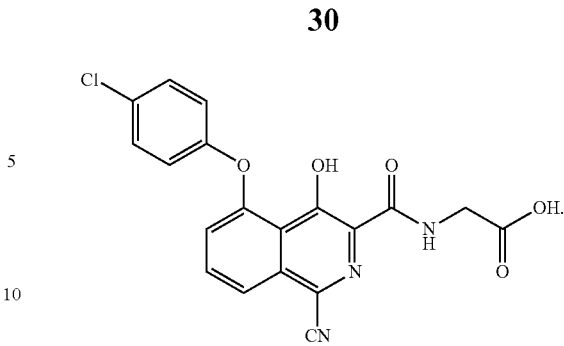

(Compound A, Form 1) characterized by having an X-ray powder diffractogram comprising a peak at 18.3°2θ±0.2°2θ, as determined on a diffractogram using Cu—Kα radiation.

2. Compound A, Form 1 of claim 1, wherein the diffractogram further comprises at least one peak selected from 7.7, 11.2, 13.8, 14.7, 15.3, 15.8, 21.1, and 22.2°2θ±0.2°2θ, as determined on a diffractogram using Cu—Kα radiation.

3. Compound A, Form 1 of claim 1, wherein the diffractogram further comprises a peak at 11.2±0.2°2θ.

4. Compound A, Form 1 of claim 3, wherein the diffractogram further comprises peaks at 7.7, 13.8, 21.1 and 22.2°2θ±0.2°2θ.

5. Compound A, Form 1 of claim 4, wherein the diffractogram is substantially as shown in FIG. 1.

6. Compound A, Form 1 of claim 1, characterized by a differential scanning calorimetry (DSC) curve that comprises an endotherm at about 251° C.

7. Compound A, Form 1 of claim 6, further comprising an exotherm at about 210° C.

8. Compound A, Form 1 of claim 7, wherein the DSC curve is substantially as shown in FIG. 2.

9. Compound A, Form 1 of claim 1, characterized by a diffractogram which is substantially as shown in FIG. 1, and by a DSC curve which is substantially as shown in FIG. 2.

10. Crystalline Form 2 of Compound A having the structure:

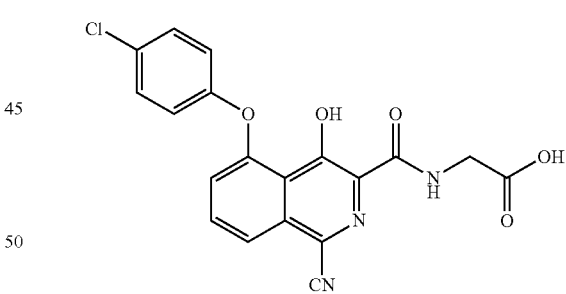

(Compound A, Form 2), characterized by having an X-ray powder diffractogram comprising a peak at 19.3±0.2°2θ, as determined on a diffractogram using Cu—Kα radiation.

11. Compound A, Form 2 of claim 10, wherein the diffractogram further comprises at least one peak selected from 8.1, 10.6, 11.5, 14.5, 16.2, 21.5, 21.9, 22.7, 24.5, and 26.6°2θ±0.2°2θ, as determined on a diffractogram using Cu—Kα radiation.

12. Compound A, Form 2 of claim 10, wherein the diffractogram further comprises peaks at 10.6 and 11.5°2θ±0.2°2θ.

13. Compound A, Form 2 of claim 12, wherein the diffractogram further comprises peaks at 14.5, 16.2, 24.5 and 26.6°2θ±0.2°2θ.

14. Compound A, Form 2 of claim 13, wherein the diffractogram is substantially as shown in FIG. 3.

15. Compound A, Form 2 of claim 10, characterized by a differential scanning calorimetry (DSC) curve that comprises an endotherm at about 249° C.

16. Compound A, Form 2 of claim 15, wherein the DSC curve is substantially as shown in FIG. 4.

17. Compound A, Form 2 of claim 10, characterized by a diffractogram which is substantially as shown in FIG. 3, and by a DSC curve which is substantially as shown in FIG. 4.

18. A pharmaceutical composition comprising a crystalline form of Compound A having the structure:

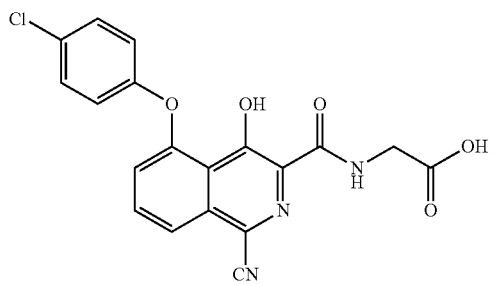

wherein the crystalline form of Compound A comprises Form 1 characterized by having an X-ray powder diffractogram comprising a peak at 18.3°2θ±0.2°2θ, as determined on a diffractogram using Cu—Kα radiation, and at least one pharmaceutically acceptable excipient.

19. The pharmaceutical composition of claim 18, wherein at least 95% of the crystalline form is Compound A, Form 1.

20. The pharmaceutical composition of claim 18, wherein at least 99% of the crystalline form is Compound A, Form 1.

21. The pharmaceutical composition of claim 18, wherein at least 99.9% of the crystalline form is Compound A, Form 1.

22. The pharmaceutical composition of claim 18, wherein at least 99.99% of the crystalline form is Compound A, Form 1.

23. A pharmaceutical composition comprising a crystalline form of Compound A, having the structure:

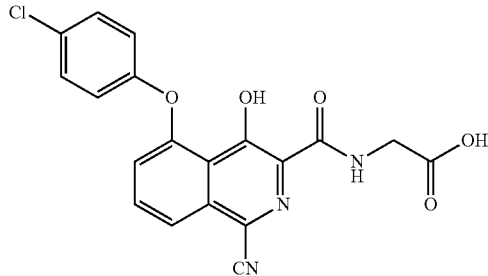

wherein the crystalline form of Compound A comprises Form 2 characterized by having an X-ray powder diffractogram comprising a peak at 19.3±0.2°2θ, as determined on a diffractogram using Cu—Kα radiation, and at least one pharmaceutically acceptable excipient.

24. The pharmaceutical composition of claim 23, wherein at least 95% of the crystalline form is Compound A, Form 2.

25. The pharmaceutical composition of claim 23, wherein at least 99% of the crystalline form is Compound A, Form 2.

26. The pharmaceutical composition of claim 23, wherein at least 99.9% of the crystalline form is Compound A, Form 2.

27. The pharmaceutical composition of claim 23, wherein at least 99.99% of the crystalline form is Compound A, Form 2.

28. The pharmaceutical composition of claim 23, wherein no more than 10% of the crystalline form is Compound A, Form 1, characterized by having an X-ray powder diffractogram comprising a peak at 18.3°2θ±0.2°2θ, as determined on a diffractogram using Cu—Kα radiation.

29. The pharmaceutical composition of claim 23, wherein no more than 1% of the crystalline form is Compound A, Form 1, characterized by having an X-ray powder diffractogram comprising a peak at 18.3°2θ±0.2°2θ, as determined on a diffractogram using Cu—Kα radiation.

30. The pharmaceutical composition of claim 23, wherein no more than 0.1% of the crystalline form is Compound A, Form 1, characterized by having an X-ray powder diffractogram comprising a leak at 18.3°2θ±0.2°2θ, as determined on a diffractogram using Cu—Kα radiation.

31. The pharmaceutical composition of claim 23, wherein no more than 0.01% of the crystalline form is Compound A, Form 1, characterized by having an X-ray powder diffractogram comprising a peak at 18.3°2θ±0.2°2θ, as determined on a diffractogram using Cu—Kα radiation.

32. The pharmaceutical composition of claim 18, wherein the composition is formulated for oral delivery.

33. The pharmaceutical composition of claim 18, wherein the composition is formulated as a tablet or a capsule.

34. The pharmaceutical composition of claim 23, wherein the composition is formulated for oral delivery.

35. The pharmaceutical composition of claim 23, wherein the composition is formulated as a tablet or a capsule.

36. A method of treating, pretreating, or delaying onset of anemia, the method comprising administering to a patient a therapeutically effective amount of a composition of claim 18.

37. A method of treating, pretreating, or delaying onset of anemia, the method comprising administering to a patient a therapeutically effective amount of a composition of claim 23.

38. A process for making crystalline Form 1 of Compound A having the structure:

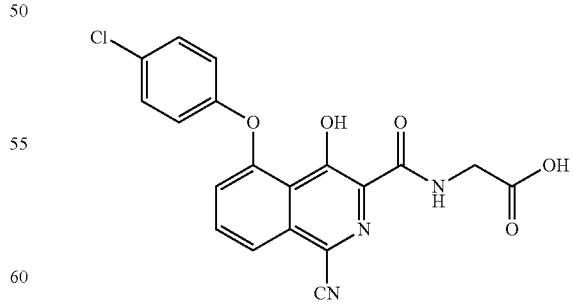

characterized by having an X-ray powder diffractogram comprising a peak at 18.3±0.2°2θ, as determined on a diffractogram using Cu—Kα radiation, comprising:
  a) heating a mixture comprising a salt of Compound A optionally in the presence of a base;

b) cooling the mixture;
c) adding an acid to the mixture; and
d) isolating Form 1 of Compound A.

39. A process for making crystalline Form 2 of Compound A having the structure:

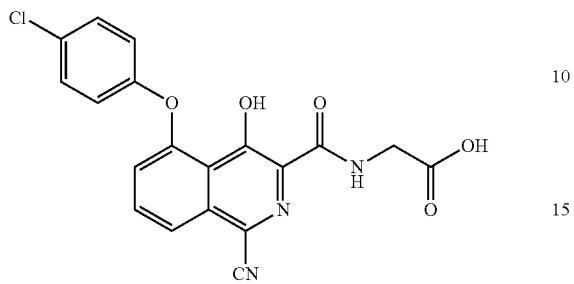

characterized by having an X-ray powder diffractogram comprising a peak at 19.3±0.2°2θ, as determined on a diffractogram using Cu—Kα radiation, comprising:
  a) heating a mixture comprising a salt of Compound A;
  b) adding an acid to the mixture and continuing heating;
  c) cooling the mixture; and
  d) isolating Form 2 of Compound A.

* * * * *